(12) United States Patent
Bunce et al.

(10) Patent No.: US 8,492,155 B2
(45) Date of Patent: Jul. 23, 2013

(54) AUTOMATED IMMUNOASSAY APPARATUS

(75) Inventors: Adrian Bunce, Worthing (GB); Andrew Fusellier, Guernsey (GB)

(73) Assignee: Dynex Technologies, Inc., Chantilly, VA (US)

( * ) Notice: Subject to any disclaimer, the term of this patent is extended or adjusted under 35 U.S.C. 154(b) by 1214 days.

(21) Appl. No.: 12/084,879

(22) PCT Filed: Nov. 10, 2006

(86) PCT No.: PCT/GB2006/004213
§ 371 (c)(1),
(2), (4) Date: Dec. 11, 2008

(87) PCT Pub. No.: WO2007/054718
PCT Pub. Date: May 18, 2007

(65) Prior Publication Data
US 2009/0155823 A1    Jun. 18, 2009

(30) Foreign Application Priority Data
Nov. 11, 2005    (GB) .................................. 0523019.8

(51) Int. Cl.
*G01N 35/04*    (2006.01)
(52) U.S. Cl.
USPC ................... 436/47; 422/63; 422/65; 436/43; 436/48

(58) Field of Classification Search
USPC ................... 422/63, 65, 66, 50, 68.1; 436/43, 436/47, 48
See application file for complete search history.

(56) References Cited

U.S. PATENT DOCUMENTS

| | | | |
|---|---|---|---|
| 6,343,906 B1 * | 2/2002 | Kraemer et al. | 414/399 |
| 6,426,050 B1 * | 7/2002 | Pham et al. | 422/561 |
| 2002/0197722 A1 * | 12/2002 | Fichera et al. | 436/43 |
| 2003/0069699 A1 | 4/2003 | Ekins et al. | |
| 2006/0073073 A1 * | 4/2006 | Fichera | 422/63 |

FOREIGN PATENT DOCUMENTS

| | | |
|---|---|---|
| DE | 3841961 | 6/1990 |
| EP | 1531328 | 5/2005 |
| FR | 2827048 | * 1/2003 |
| JP | 58102161 | 6/1983 |
| JP | 59116044 | 7/1984 |
| WO | 92/11538 | 7/1992 |
| WO | 2005098454 | 10/2005 |

* cited by examiner

*Primary Examiner* — P. Kathryn Wright
(74) *Attorney, Agent, or Firm* — Diederiks & Whitelaw PLC

(57) ABSTRACT

An automated immunoassay apparatus is disclosed comprising a single optical reading device (2a, 2b) for reading two microtitre plates (9, 14). A first microtitre plate (9) is loaded into an upper plate holder (8) which is linearly translated at a fixed height. A second microtitre plate (14) is loaded into a lower plate holder (13). The lower plate holder (13) runs along a contoured track which varies the vertical height of the second microtitre plate (14).

12 Claims, 19 Drawing Sheets

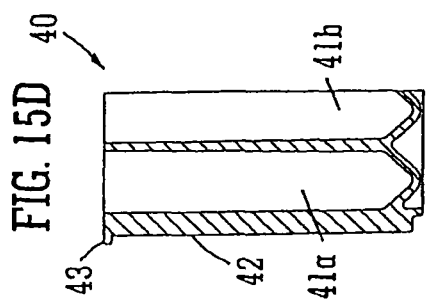
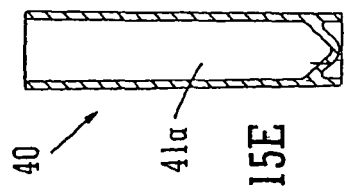
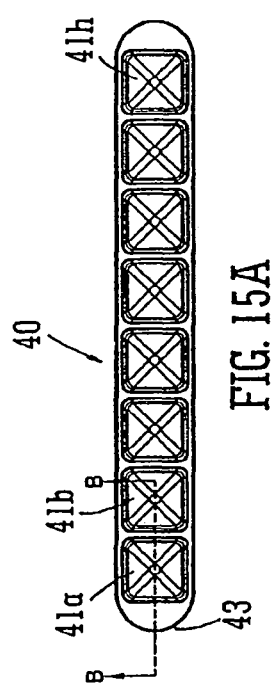
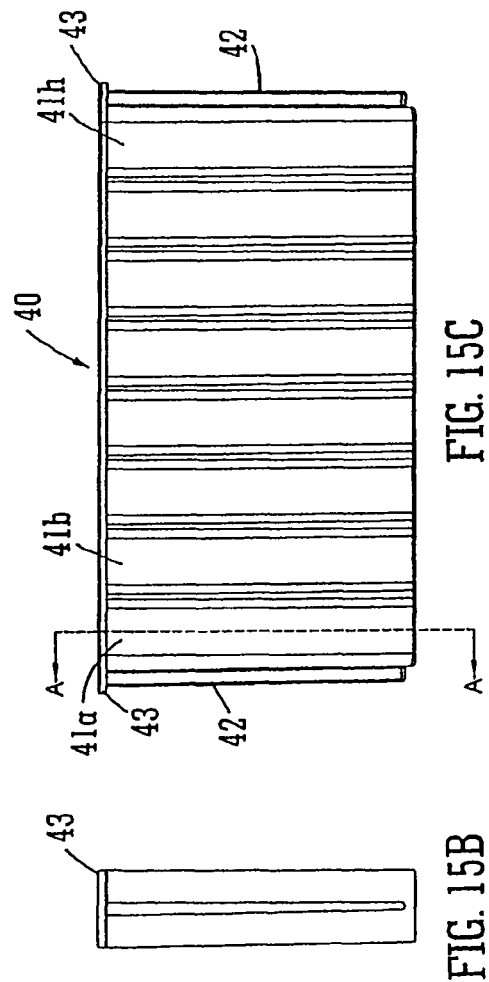

AUTOMATED IMMUNOASSAY APPARATUS

CROSS-REFERENCE TO RELATED APPLICATIONS

The present application represents a National Stage application of PCT/GB2006/004213 filed Nov. 10, 2006 entitled "Automated Immunoassay Apparatus", pending.

The present invention relates to an automated immunoassay apparatus, an Enzyme Linked ImmunoSorbent Assay system, a method of reading microtitre plates, a deep well or dilution strip and a dilution strip holder.

The preferred embodiment relates to automated immunoassay apparatus for carrying out diagnostic testing and in particular to apparatus for carrying out Enzyme Linked ImmunoSorbent Assay ("ELISA") procedures.

A number of different testing techniques for biological products are known and these include latex consumable tests and Polymerase Chain Reaction ("PCR") tests.

Latex consumable tests are used, for example, in home pregnancy testing kits and are fast, reasonably accurate but are comparatively expensive.

PCR tests are used mainly in research environments. Custom-made equipment is usually required in order for the technique to be reliably reproduced by laboratory technicians. Such equipment is comparatively expensive and is not generally compatible with other manufacturers' equipment.

Immunoassay procedures are a preferred way of testing biological products. These procedures exploit the ability of antibodies produced by the body to recognise specific antigens which may, for example, be associated with foreign bodies such as bacteria or viruses, or with other body products such as hormones. Once a specific antigen has been detected by an antibody this can be indicated as a positive sample preferably by using fluorescent or chemiluminescent markers or less preferably by using radioactive markers. Radioactive markers are less preferred due to environmental and safety concerns regarding their handling, storage and disposal.

ELISA is a particularly preferred form of immunoassay procedure wherein antibodies are linked to an insoluble carrier surface such as a sample vessel. The antibodies are used to capture any counterpart antigens which may be present in a sample solution. If antigens are present then these bond with the antibodies to form antigen-antibody complexes. Substances known as "enzyme conjugates" are then added to the sample. An enzyme conjugate contains an enzyme which covalently bonds with the antigen part of any antigen-antibody complexes which have been formed. Colourless reagents are then added to the sample which are broken down in the presence of the enzyme to produce a distinctive colour. The colour strength is photometrically determined to advantageously give a quantitative indication of the number of antibody-antigen complexes which have been formed. This in turn gives an indication of the number of specific antigens present per unit volume of sample fluid.

Another advantage of ELISA procedures is that they do not suffer from the storage and disposal problems associated with radioimmunoassays.

Although it is common to look for specific antigens in a sample, it is also possible to look for specific antibodies which are produced by the body in response to an infection. In such cases, the detection of a large number of specific antibodies in a sample will indicate that a large number of corresponding antigens are also present. For example, a Rubella infection will result in the production by the body of a large number of antibodies to Rubella antigenic material. The detection of these antibodies in large numbers would indicate that the patient has been exposed to Rubella antigenic material.

Although other different testing procedures are available, ELISA remains one of the most commonly used because it is relatively inexpensive, has a high throughput and has good performance. There is also widespread availability of consumables and instrumentation required for the process.

Early known ELISA systems were run manually and samples and dispensing reagents were transferred manually using pipettes. Sample containers were washed under a tap and the results were measured visually. However, as can be appreciated, manually operated systems suffered from a number of problems including variable results with a limited dynamic range. The technician was also unduly exposed to potentially biohazardous material.

In recent years systems have been developed which automate many of the steps (or "phases") involved in the ELISA procedures such as sample distribution, dilution, incubation, washing, enzyme conjugate addition, reagent addition, reaction stopping and the analysis of results.

Automated immunoassay apparatus for carrying out ELISA procedures are widely used in clinical laboratories of e.g. pharmaceutical companies, hospitals and universities for in-vitro diagnostic applications such as testing for diseases and infection, and for assisting in the production of new vaccines and drugs.

Automated ELISA systems use a standard sample vessel known as a microplate which can be stored easily and which may be used with a variety of biological specimens. Microplates manufactured by the Applicants are sold under the name "MICROTITRE"®. However, the ELISA system described in the present application is designed to be an open system thereby allowing other manufacturers' microplates and other consumables to be used.

Microplates have been commercially available since the 1960s and consist of a reusable plate made from e.g. polystyrene, PVC, Perspex or Lucite and measuring approximately 5 inches (12.7 cm) in length, 3.3 inches (8.5 cm) in width, and 0.55 inches (1.4 cm) in depth.

Microplates made from polystyrene are particularly preferred on account of polystyrene's enhanced optical clarity which assists visual interpretation of the results of any reaction. Polystyrene microplates are also compact, lightweight and easily washable.

Known microplates comprise 96 wells or indentations (also commonly known as "microwells") which are symmetrically arranged in an 8×12 array. Each microwell of a microplate will normally contain a sample from a different patient. The microwells are sometimes also referred to as the "solid phase" since they are considered to be the starting point upon which the rest of the testing procedures are based.

Microwells typically have a maximum volume capacity of approximately 350 µl. However, normally only 10-100 µl of fluid is dispensed into a microwell.

Microplates having a flat-bottomed well geometry are widely accepted for bacteriology and other microbiology applications including tissue culture growth analysis and antibiotic sensitivity testing. Microplates having "U" and "V" shaped well bottom geometries are also known and are used in complement fixation analysis so as to accommodate agglutination applications. "U" and "V" shaped microwells are effective in reducing the sample and reagent volume requirements and they also help concentrate the reaction in the well bottom thereby aiding the subsequent interpretation of results. Flexible microplates made from polyvinyl chloride (PVC) are used in radioimmunoassays. These microplates are produced in the standard 96-well format.

A number of different variations of the ELISA technology are commercially available. However, all require that fluid samples, e.g. blood, serum, urine, etc., are aspirated from a sample tube and are then dispensed into a microwell of a microplate. Samples may be diluted prior to being dispensed into microplates or they may be dispensed into deep well microplates and diluted in situ.

ELISA kits are commercially available which consist of microplates having microwells which have been coated by the manufacturer with a specific antibody (or antigen). For example, in the case of a Rubella diagnostic kit, the kit manufacturer will dispense Rubella antibodies which have been suspended in a fluid into the microwells of a microplate. The microplate is then incubated for a period of time, during which time the antibodies adhere to the walls of the microwells up to the fluid fill level (typically about half the maximum fluid capacity of the microwell). The microwells are then washed leaving a microplate having microwells whose walls are uniformly covered with Rubella antibodies up to the fluid fill level.

A testing laboratory will receive a number of sample tubes containing, for example, body fluid from a number of patients. A specified amount of fluid is then aspirated out of the sample tube using a pipette mechanism and is then dispensed into one or more microwells of a microplate which has been previously prepared by the manufacturer as discussed above. If it is desired to test a patient for a number of different diseases then fluid from a patient may be dispensed into a number of separate microplates. Each microplate can then be tested for the presence of a different disease.

The pipette mechanism used to aspirate and dispense fluid samples uses disposable tips which are ejected after being used so as to prevent cross-contamination of patients' samples.

Once the desired number of patients' samples have been dispensed into a microplate, the microplate is then placed in an incubator which speeds up the process of binding or antigen uptake (if applicable). Preferred incubation temperatures and incubation times are specified by the testing kit manufacturer. Incubation temperatures at around body temperature (37° C.) are common, but different incubation temperatures may be used. The maximum incubation temperature is normally around 55° C. The incubation process may last around half an hour, although incubation times of up to a few hours may sometimes be necessary.

After incubation the microplate may then be transferred from the incubator to a washer unit where all the microwells are thoroughly washed. Washing involves repeatedly filling the microwells with an inert fluid/detergent mixture ("wash buffer" solution). The fluid/detergent mixture is then aspirated out of all the microwells. Typically, five fill/aspirate cycles per microwell are required in order to wash sufficiently the microwells. The washing process is usually achieved by filling and aspirating through a manifold thereby allowing whole columns or rows of microwells to be filled/aspirated at the same time.

The wash fluid is usually supplied by the kit manufacturer and is intended to wash the microplate without damaging any antigen-antibody complexes which have been formed during the incubation phase. The washing phase is intended to remove any unbound proteins that would otherwise interfere with the subsequent analytical processes whilst leaving the antigen-antibody complexes intact.

Washing typically lasts around 5 minutes and can take place independently of other steps which might be required on other microplates. Failure to wash the microplate after sample incubation would de-sensitise the process as the fluid content of the sample needs to be removed for subsequent reagent additions to take place.

At the end of the washing phase the microwells are left empty apart from any antigen-antibody complexes that have formed. At this stage there is no visible difference between a negative and a positive sample.

At this stage the ELISA procedure has successfully emulated the immune system by capturing antigens suspended in a sample in-vitro. Antibodies which have been coated to the walls of the microplate during manufacture have, in the case of a positive sample, bonded to antigens present in the patient's sample.

The next stage in the ELISA procedures is to add an enzyme conjugate to the microwell that will attach or bind to the antigen part but not to the antibody part of any antigen-antibody complex which has been formed. Therefore, in the case of a negative sample where no antigen-antibody complexes have been formed and hence there is no antigenic material left in the microwell, then there is nothing for the enzyme conjugate to bind on to.

Once enzyme conjugate has been added to a sample the microplate is then usually placed once again in an incubator in order to accelerate any binding of the enzyme to the antigen part of any antigen-antibody complex. This further incubation step may take around 30 minutes.

Once the enzyme conjugate has been added and the microplate has been left to incubate, the microplate is then removed from the incubator and is washed once more. This time the microplate is washed to remove any unbound enzyme conjugate material. This will therefore either leave antigen-antibody complexes together with bound enzyme conjugate (in the case of a positive sample) or just the factory bound antibody (in the case of a negative sample).

The next stage in the diagnostic process is to add a fixed volume of a reagent (also known as a "substrate") to each microwell and optionally return the microplate to the incubator a yet further time. Alternatively, the microplate may simply be left to incubate at ambient room temperature.

Reagents, upon contact with the enzyme conjugate bound to the antigen part of any antigen-antibody complexes which are present, break down giving off a distinctive colour which typically has a narrow band wavelength. The breakdown of the reagent and the subsequent colour development usually reaches saturation after about 30 minutes. Once colour development has been satisfactorily completed, the microplates may be washed again. If the microplate were not washed after enzyme conjugate had been added then this would allow the enzyme conjugate to mix freely with reagent which is added at the next stage. This would result in colour being produced for all samples regardless of the presence of antigen-antibody complexes.

Enzyme conjugates and reagents (substrates) must be carefully chosen. The same reagent is often used for multiple analytes, i.e. Rubella, Hepatitis, HIV, etc., but the enzyme conjugate is usually unique to the target analyte.

The process of incubating, adding reagent and washing may be repeated a number of times and different reagent types, incubation temperatures and wash parameters may be used on subsequent cycles.

Once any colour development has reached saturation, the microplates are then ready for interpretation. Acid may be added to prevent further colour development and this also has the advantage of leaving the microplate stable for a number of hours after the reaction has been stopped. The acid used is normally common across kits.

After the reaction has been stopped, the microplates are then interpreted by transferring the microplates to an optical reader which photometrically measures the amount of colour in each microwell. Narrow-band light is projected through each microwell and the transmitted light is measured. This enables the amount of absorption to be quantified and a corresponding output signal is produced. Results may then be sent to a host computer.

Alternatively, luminescent or fluorescent effects may be used, in which case light emission rather than light absorption is measured and quantified.

Controls and standards are also typically supplied by the kit manufacturer together with indications of expected results.

Controls are generally supplied with a qualitative kit such as Hepatitis testing and are used for quality control and to provide a relative cut-off. A few negative controls and normally one positive control are provided with the kit and are expected to give results within a range previously determined by the kit manufacturer. Following the reading of the microplate after substrate development, the results of the controls are checked. The positive control is checked to see if it has been reported as a positive result and the negative controls are checked to see if they are below a certain value. Results from controls that are within the manufacturers published acceptance criteria indicate that the kit and the testing process have worked correctly. The controls also provide a relative cut-off. For example, if the highest negative control is reported with a value of 0.5 then the kit instructions might indicate that any result above 0.5 should be expressed as a positive result. As the controls have been run on the same microplate as the samples being tested, this method provides a relative cut-off which compensates for any influencing factors associated with the process.

Standards are provided in order to give an expected result. They are usually used to build a standard curve for assays that require a quantitative result. For example, six standards having a different known concentration of analyte may be provided. By plotting on a graph the measured result (e.g. colour intensity) for each standard on the Y axis against the known concentration on the X axis, a curve of measured result versus concentration can be drawn up. This enables an unknown sample (which is usually processed on the same microplate) to be correlated against the curve so that the measured result can be expressed as a concentration.

Known automated immunoassay systems use a pipette mounted on a first arm to aspirate and dispense fluid. A second separate arm is then used to move microplates from one process stage (e.g. incubation, washing etc.) to another. Such a system requires the provision of multiple drive mechanisms—one to move the pipette around and another to move the microplates around. This results in a relatively complex, large and hence correspondingly expensive system.

According to an aspect of the present invention there is provided an automated immunoassay apparatus comprising:

a first mechanism for moving or translating a first microtitre plate;

a second mechanism for moving or translating a second different microtitre plate;

wherein the automated immunoassay apparatus further comprises:

a single reading device for reading both the first and the second microtitre plates.

The first mechanism preferably comprises a substantially straight or substantially linear drive mechanism for moving or translating the first microtitre plate forwards and/or backwards along a first axis.

The first mechanism is preferably arranged and adapted to maintain the first microtitre plate at substantially a constant height along at least 5%, 10%, 15%, 20%, 25%, 30%, 35%, 40%, 45%, 50%, 55%, 60%, 65%, 70%, 75%, 80%, 85%, 90%, 95% or 100% of the length of the first axis.

The first mechanism preferably comprises one or more rods or linear guide tracks and one or more first devices or bearing blocks which are arranged and adapted to slide or translate in use along the one or more rods or linear guide tracks.

The apparatus preferably further comprises a first microtitre plate holder attached or connected to the one or more first devices or bearing blocks, wherein a first microtitre plate is positioned, placed or loaded in use on the first microtitre plate holder. A first drive belt or other device for driving and/or translating the one or more first devices or bearing blocks and/or the first microtitre plate holder is preferably provided.

According to an embodiment there is preferably provided a first motor for driving and/or translating the first drive belt or other device.

The first mechanism is preferably arranged and adapted so as to pass a first microtitre plate at a distance or separation of x mm relative to the reading device, wherein x is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

In a mode of operation the first mechanism is preferably arranged to present or position the first microtitre plate in a first position such that the first microtitre plate may be removed and/or replaced by a robotic arm or other device.

The apparatus preferably further comprises dispensing means for dispensing a sample to the first microtitre plate when the first microtitre plate is positioned in the first position.

The apparatus preferably further comprises aspirating means for aspirating a sample from the first microtitre plate when the first microtitre plate is positioned in the first position.

The apparatus preferably further comprises washing means for washing the first microtitre plate when the first microtitre plate is positioned in the first position.

According to an embodiment in a mode of operation the first mechanism is preferably arranged to present or position the first microtitre plate in a second position such that the first microtitre plate may be read by the reading device.

According to an embodiment in a mode of operation the first mechanism is preferably arranged to present or position the first microtitre plate in a third position such that the first microtitre plate is positioned within an incubator.

According to an embodiment the second mechanism preferably comprises a substantially straight or substantially linear drive mechanism for moving or translating the second microtitre plate forwards and/or backwards along a second axis. The second mechanism is preferably arranged and adapted to vary the height of the second microtitre plate along at least 5%, 10%, 15%, 20%, 25%, 30%, 35%, 40%, 45%, 50%, 55%, 60%, 65%, 70%, 75%, 80%, 85%, 90%, 95% or 100% of the length of the second axis.

The second mechanism preferably comprises one or more rods or linear guide tracks and one or more second devices or bearing blocks which are arranged and adapted to slide or translate in use along the one or more rods or linear guide tracks.

According to the preferred embodiment the apparatus preferably further comprises a second microtitre plate holder attached or connected to the one or more second devices or bearing blocks, wherein a second microtitre plate is positioned, placed or loaded in use on the second microtitre plate holder. A second drive belt or other device for driving and/or translating the one or more second devices or bearing blocks and/or the second microtitre plate holder is preferably provided.

One or more pivoting arms preferably connect the one or more second devices or bearing blocks to the second microtitre plate holder. The one or more pivoting arms preferably comprise four pivoting arms which preferably form in use a parallelogram with the second microtitre plate holder and the second devices or bearing blocks. The one or more pivoting arms are preferably arranged and adapted to ensure that the second microtitre plate holder remains substantially horizontal in use.

The second microtitre plate holder preferably comprises one or more guide wheels.

The apparatus preferably further comprises a contoured track and wherein the one or more guide wheels attached to the second microtitre plate holder are arranged to follow or track the contoured track. The contoured track in combination with the one or more guide wheels is preferably arranged to cause the second microtitre plate holder to be raised and lowered in height. The contoured track preferably has a plateau or substantially horizontal region. The contoured track preferably has a first ramp portion or section leading to and/or from the plateau or substantially horizontal region. The contoured track preferably has a second different ramp portion or section leading to and/or from the plateau or substantially horizontal region. The second ramp portion or section is preferably arranged on an opposite or opposed side of the plateau or substantially horizontal region to the first ramp portion or section.

The reading device is preferably arranged or disposed adjacent or towards or at the centre of the plateau or substantially horizontal region.

The second mechanism is preferably arranged and adapted so as to pass the second microtitre plate at a distance or separation of y mm relative to the reading device, wherein y is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

According to an embodiment in a mode of operation the second mechanism is arranged to present or position the second microtitre plate in a first position such that the second microtitre plate may be removed and/or replaced by a robotic arm or other device.

The apparatus preferably further comprises dispensing means for dispensing a sample to the second microtitre plate when the second microtitre plate is positioned in the first position.

The apparatus preferably further comprises aspirating means for aspirating a sample from the second microtitre plate when the second microtitre plate is positioned in the first position.

The apparatus preferably further comprises washing means for washing the second microtitre plate when the second microtitre plate is positioned in the first position.

According to an embodiment in a mode of operation the second mechanism is arranged to present or position the second microtitre plate in a second position such that the second microtitre plate may be read by the reading device.

According to an embodiment in a mode of operation the second mechanism is arranged to present or position the second microtitre plate in a third position such that the second microtitre plate is positioned within an incubator.

The reading device preferably comprises one or more optical transmitters. The one or more optical transmitters preferably comprise one or more lamps, lasers, light emitting diodes or light emitting devices. The one or more optical transmitters preferably further comprises one or more components selected from the group consisting of: (i) one or more optical infra-red heat filters; (ii) one or more filters; (iii) one or more optic fibres; (iv) one or more lenses; and (v) one or more optical stops.

The reading device preferably comprises an array of 12 photo-emitters for illuminating a row of 12 wells of a microtitre plate. The reading device preferably further comprises one or more reference light sources, photo-emitters or channels.

The reading device preferably further comprises one or more optical receivers. The one or more optical receivers preferably comprise one or more photodiodes or photo-detectors.

The one or more optical receivers preferably further comprise one or more components selected from the group consisting of: (i) one or more lenses; and (ii) one or more optical stops.

The reading device preferably comprises an array of 12 photo-detectors for detecting a plurality of light beams which have passed through a row of 12 wells of a microtitre plate.

The reading device preferably further comprises one or more reference photo-detectors or channels.

According to an embodiment the apparatus may further comprise a third mechanism for moving or translating a third different microtitre plate relative to the reading device.

According to an embodiment the apparatus may further comprise a fourth mechanism for moving or translating a fourth different microtitre plate relative to the reading device.

According to the preferred embodiment the apparatus further comprises one or more incubators.

According to another aspect of the present invention there is provided an Enzyme Linked ImmunoSorbent Assay ("ELISA") system comprising an automated immunoassay apparatus as described above.

According to another aspect of the present invention there is provided a method of reading microtitre plates comprising:

using a first mechanism to move or translate a first microtitre plate relative to a single reading device;

using a second mechanism to move or translate a second different microtitre plate relative to the single reading device; and reading the first microtitre plate and the second microtitre plate using the same single reading device.

According to another aspect of the present invention there is provided assay apparatus comprising:

one or more first sliding or translating devices or first bearing blocks for sliding along one or more rods, guide rails or tracks, the one or more first sliding or translating devices or first bearing blocks being attached to a first microtitre plate holder; and one or more second sliding or translating devices or second bearing blocks for sliding along one or more rods, guide rails or tracks, the one or more second sliding or translating devices or second bearing blocks being connected to a second microtitre plate holder via one or more intermediate pivoting arms such that the height of the second microtitre plate holder may be varied or changed in use.

The second microtitre plate holder preferably comprises one or more guide wheels, rollers or devices for engaging with one or more paths, tracks or guides. The one or more paths, tracks or guides preferably have a vertical profile which varies along the axial length of the one or more paths, tracks or guides.

Preferably, when the one or more guide wheels, rollers or devices engage with the one or more paths, tracks or guides the vertical height of the second microtitre plate is caused to vary.

The first microtitre plate holder and the second microtitre plate holder are preferably arranged to pass over, through or across the same reading device. The reading device is preferably arranged to measure the optical density of samples in a first microtitre plate loaded on the first microtitre plate holder and a second microtitre plate loaded on the second microtitre plate holder.

According to another aspect of the present invention there is provided an automated clinical-diagnostic workstation arranged and adapted to simultaneously process at least two microtitre plates. The workstation preferably comprises a track which varies in height and wherein a microtitre plate holder is arranged and adapted to move along the track so as to raise and lower, in use, the height and/or position of a microtitre plate loaded into the microtitre plate holder.

According to another aspect of the present invention there is provided an automated workstation comprising means for driving a sliding device along a linear path, guide rod or track whilst causing a microtitre plate holder connected or coupled to the sliding device to be raised up towards a device for optically reading sample wells of a microtitre plate and/or lowered down from a device for optically reading sample wells of a microtitre plate.

According to another aspect of the present invention there is provided an automated workstation comprising:

a first device for translating a first microtitre plate holder and associated microtitre plate along a first path over an optical reader, the first path having a first section, a second section and a third section;

a second device for translating a second microtitre plate holder and associated microtitre plate along a second path over the same optical reader, the second path having a first section, a second section and a third section;

wherein the first and third sections of the first and second paths are substantially vertically separated from one another and wherein the second sections of the first and second paths are at substantially the same vertical height and/or substantially overlap and/or are substantially co-planar.

According to another aspect of the present invention there is provided a deep well or dilution strip for use in an automated immunoassay apparatus, wherein the deep well or dilution strip comprises an 8×1 array or arrangement of dilution wells wherein the dilution wells have a substantially rectangular cross section and a maximum volume in the range 1.8 to 2.5 ml and wherein the dilution wells have an internal depth or height in the range 35 to 45 mm.

The dilution wells preferably have a maximum volume selected from the group consisting of: (i) 1.8-1.9 ml; (ii) 1.9-2.0 ml; (iii) 2.0-2.1 ml; (iv) 2.1-2.2 ml; (v) 2.2-2.3 ml; (vi) 2.3-2.4 ml; and (vii) 2.4-2.5 ml.

The dilution wells preferably have an internal depth or height selected from the group consisting of: (i) 35-36 mm; (ii) 36-37 mm; (iii) 37-38 mm; (iv) 38-39 mm; (v) 39-40 mm; (vi) 40-41 mm; (vii) 41-42 mm; (viii) 42-43 mm; (ix) 43-44 mm; and (x) 44-45 mm.

According to another aspect of the present invention there is provided a deep well or dilution strip for use in an automated immunoassay apparatus. The deep well or dilution strip preferably comprises an 8×1 array or arrangement of dilution wells.

Each dilution well preferably has an internal depth measured from the top of the deep well or dilution strip to the bottom of each dilution well of 38.5±1.0 mm.

The deep well or dilution strip preferably has an external height of 39.8±1.0 mm.

One or more of the dilution wells preferably have a bottom portion selected from the group consisting of: (i) substantially flat; (ii) rounded or curved; (iii) an inverted three or four sided pyramid; and (iv) a multi-faceted bottom.

According to an embodiment the deep well or dilution strip comprises an upper lip portion.

According to an embodiment the deep well or dilution strip comprises one, two or more than two projections for engaging with a slot, slip or aperture in a dilution strip holder.

According to another aspect of the present invention there is provided a dilution strip holder in combination with a deep well or dilution strip as described above.

The preferred embodiment relates to an automated immunoassay apparatus which enables two microtitre plates to be processed using a single reading device. Advantageously, the footprint of the preferred automated immunoassay apparatus is substantially the same as a conventional apparatus which is only able to process and read a single microtitre plate.

The preferred automated immunoassay apparatus preferably enables two microtitre plates to be processed within the preferred apparatus without requiring a robotic arm to be activated to remove a first microtitre plate which has been read and to replace it with a second microtitre plate to be processed and read.

The preferred immunoassay apparatus is preferably arranged to pass two microtitre plates containing samples through a single optical reading device. The optical reading device preferably emits a plurality of optical beams having a specific wavelength. The optical beams preferably pass through a row of wells in the microtitre plate. The optical beams are then preferably detected by a row of photo-detectors which are preferably mounted above the microtitre plate being read. The optical density of the samples in the row of the microtitre plate being read can then preferably be determined.

The preferred immunoassay apparatus preferably ensures that both microtitre plates are able to pass through the optical reading device at substantially the same height.

The preferred immunoassay apparatus preferably enables in one mode of operation two microtitre plates to be positioned or presented towards the front of the preferred apparatus such that at least one or both of the microtitre plates can then be accessed by a robotic arm or other means.

According to the preferred embodiment two or more microtitre plates can be moved or translated substantially independently of one another within the preferred immunoassay apparatus so that each microtitre plate can preferably be moved to different locations or modules within the preferred immunoassay apparatus.

The preferred automated immunoassay apparatus preferably comprises a first or upper plate drive mechanism which preferably comprises a straight or linear drive for translating a first or upper microtitre plate holder holding a first or upper microtitre plate. The height of the first or upper microtitre plate preferably remains constant.

A particularly preferred aspect of the present invention is that the preferred immunoassay apparatus preferably comprises a second or lower microtitre plate holder for a second or lower microtitre plate. The height of the second or lower microtitre plate can preferably be altered or raised. The preferred apparatus preferably ensures that the second or lower microtitre plate preferably passes through or across the single reading device at substantially the same fixed height as the first or upper microtitre plate.

Various embodiments of the present invention will now be described, by way of example only, and with reference to the accompanying drawings in which:

FIG. 1A shows the general layout of an automated immunoassay apparatus according to a preferred embodiment of the present invention and shows a first or upper microtitre plate and a second or lower microtitre plate positioned generally towards the front of the apparatus and FIG. 1B shows in greater detail the first or upper microtitre plate and the second or lower microtitre plate and part of their associated drive mechanisms;

Figure 8:
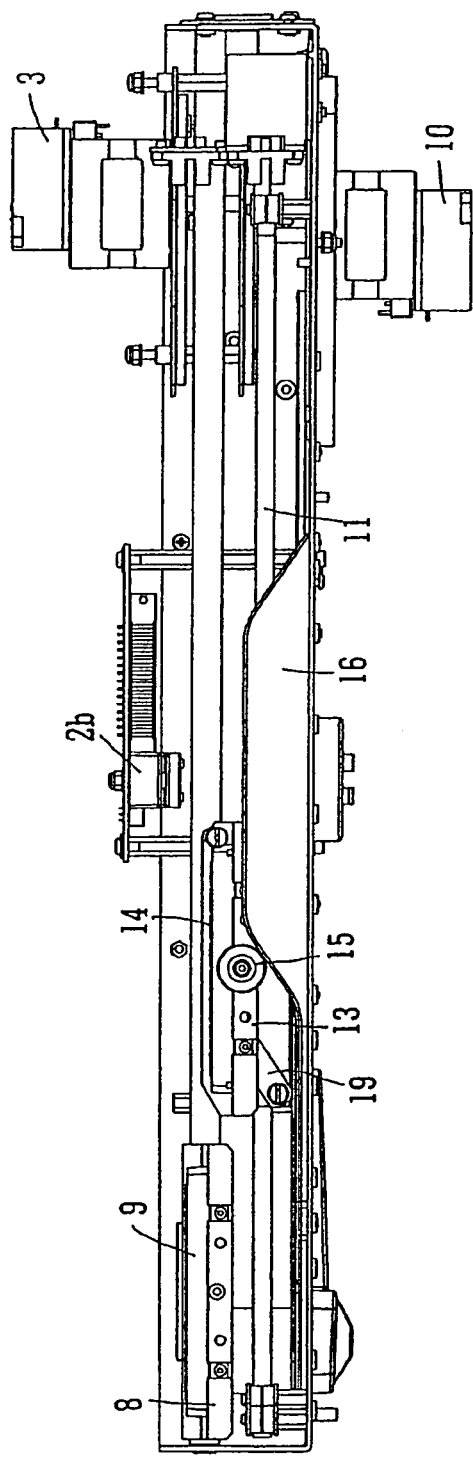
Figure 9:
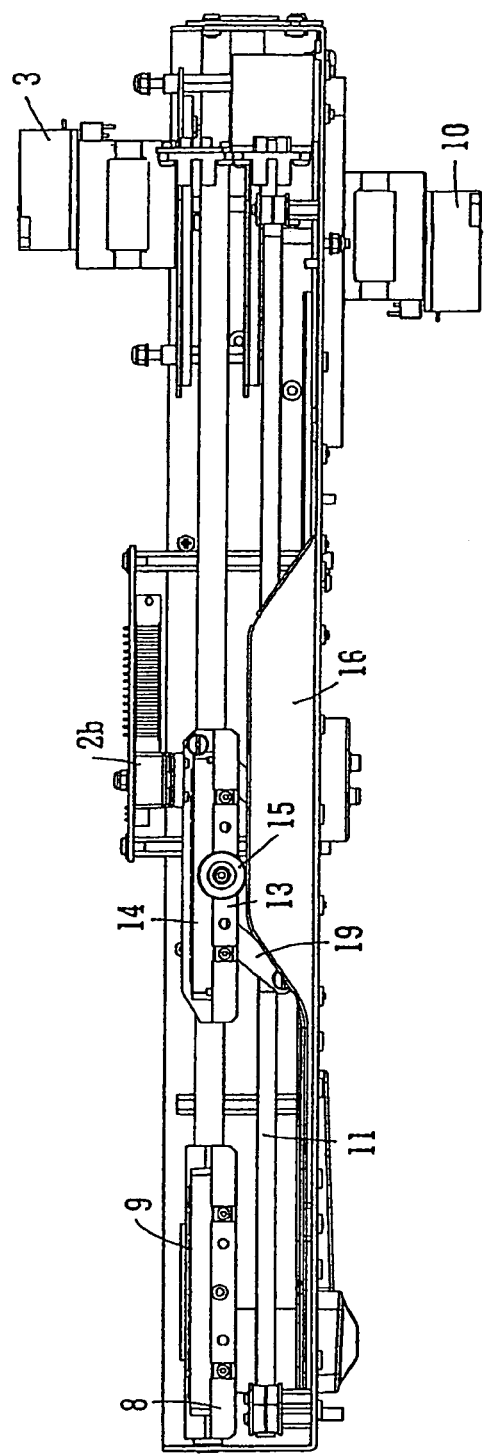
Figure 10:
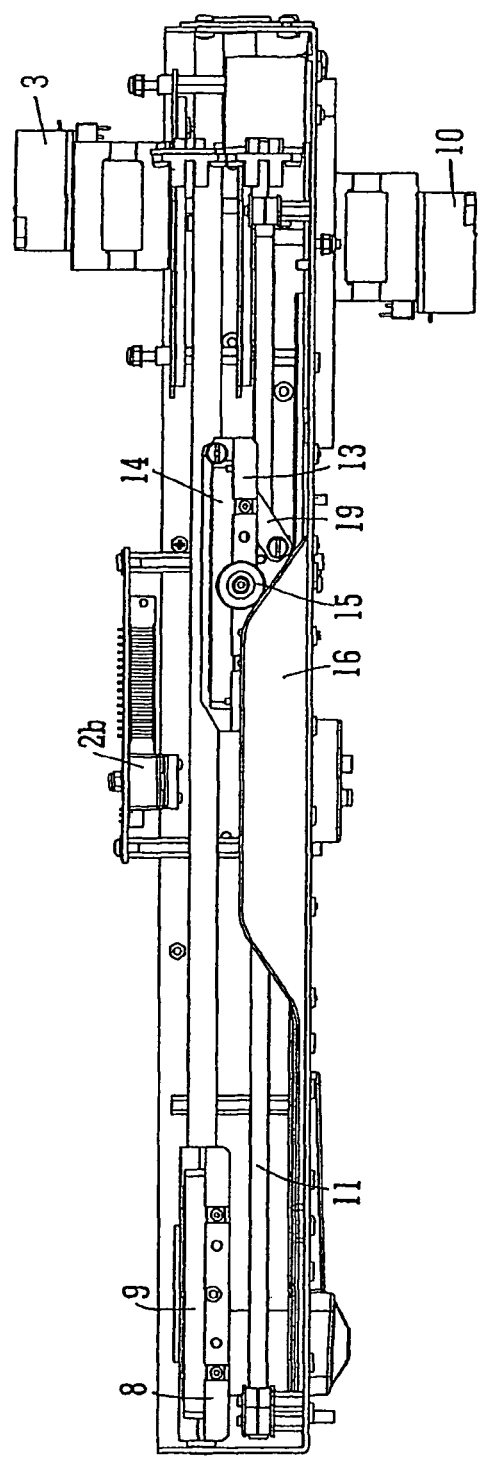
Figure 11:
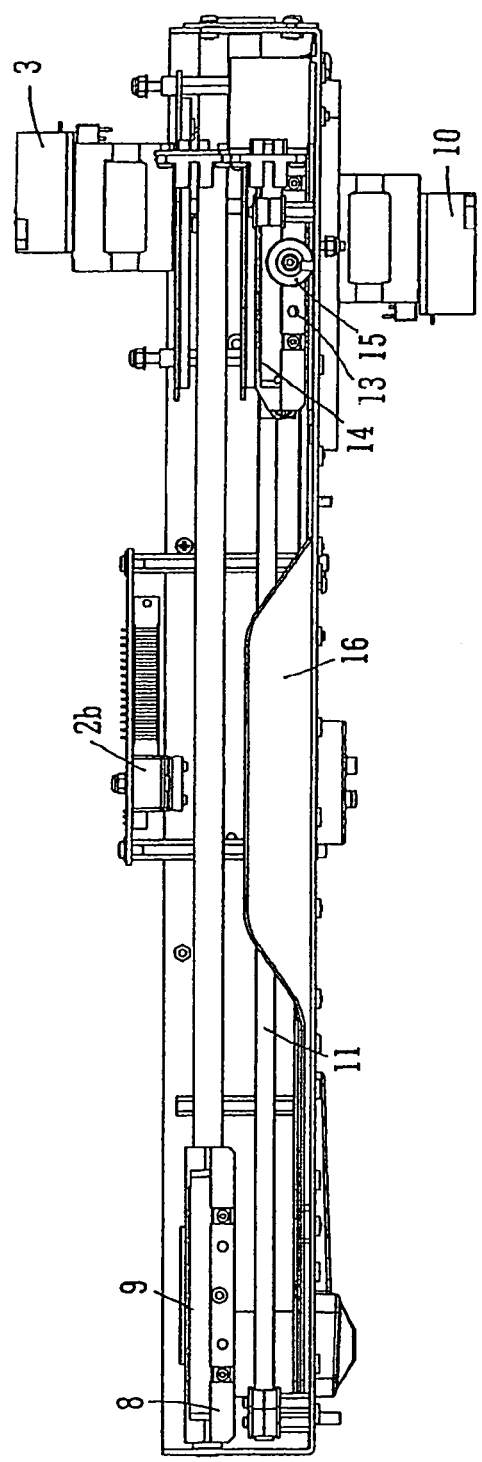
Figure 12:
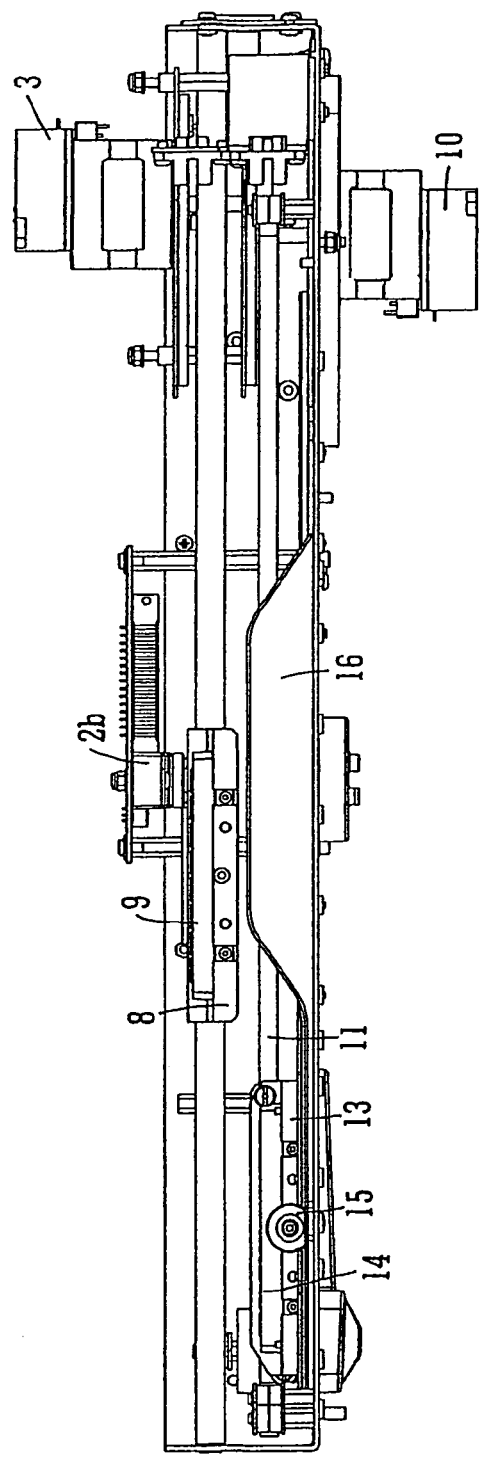
Figure 13A:
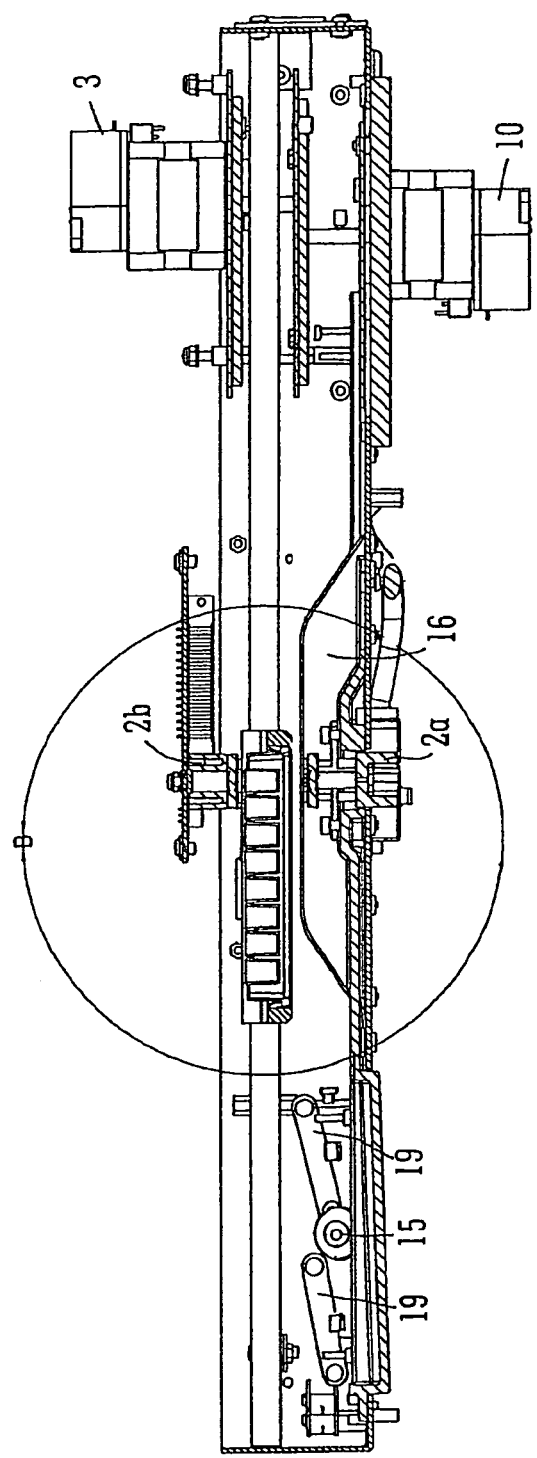
Figure 13B:
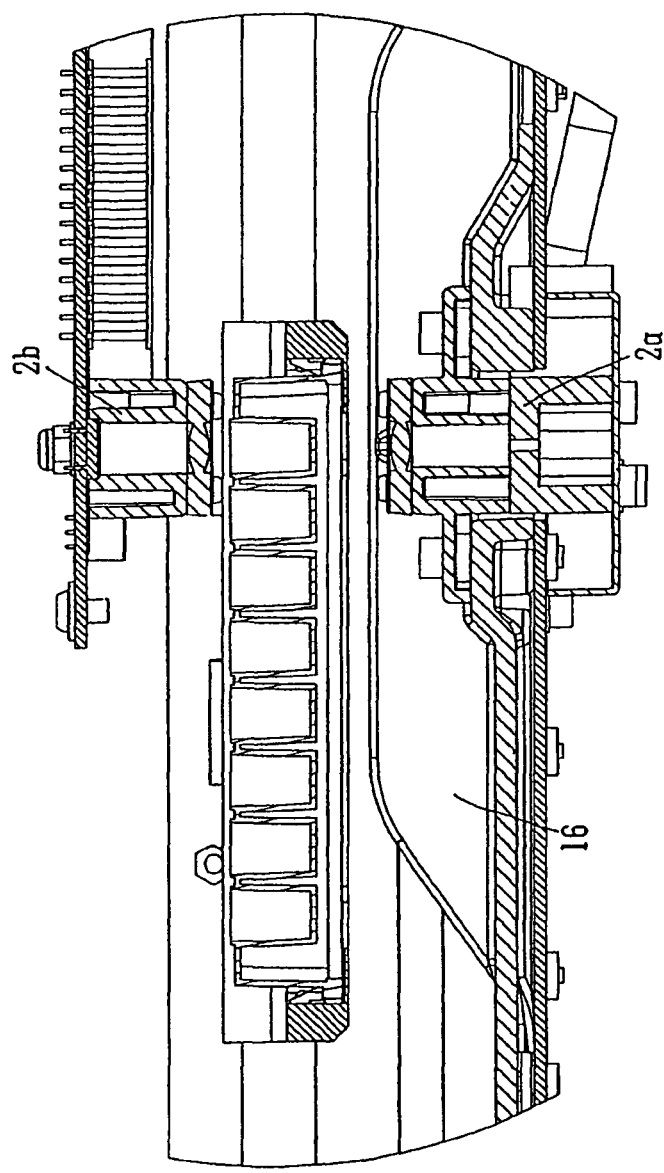
Figure 14B:
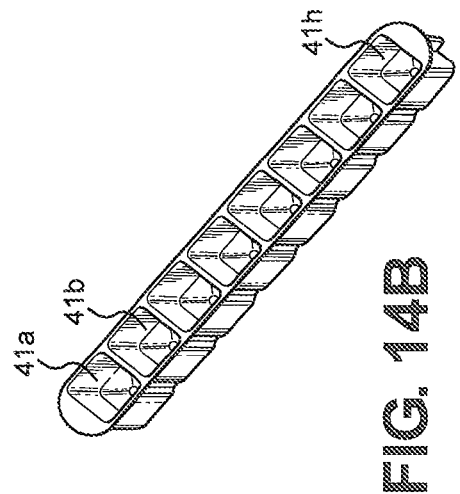
Figure 14C:
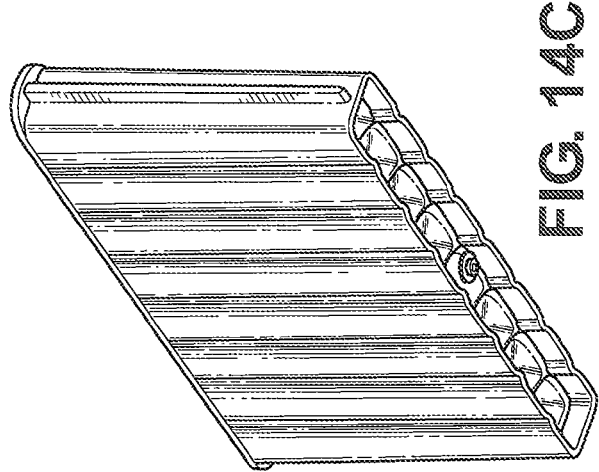
Figure 14A:
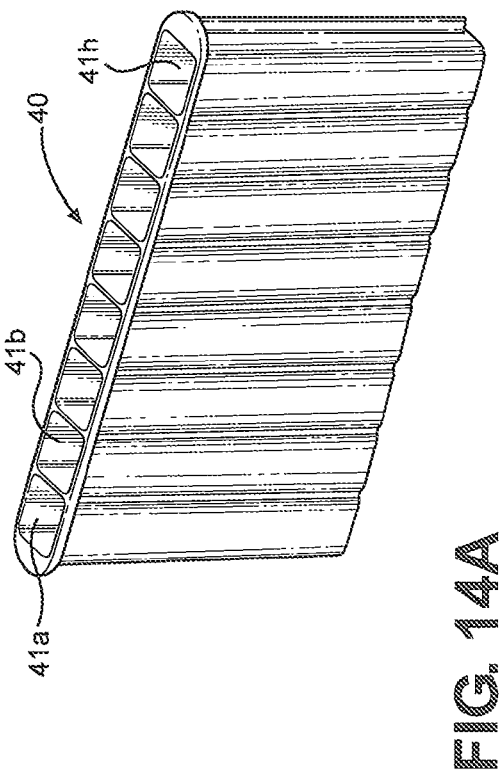
Figure 16:
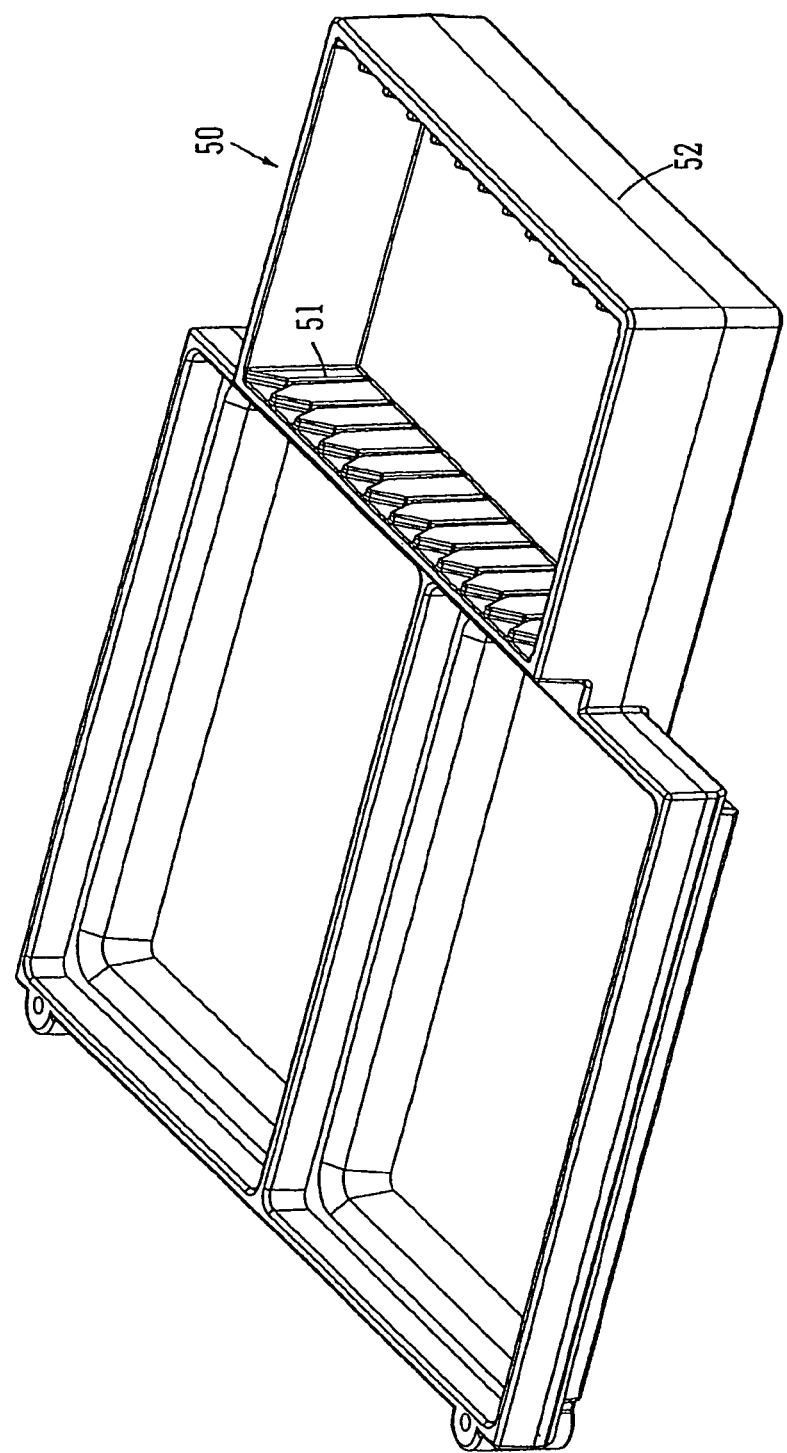
Figure 17:
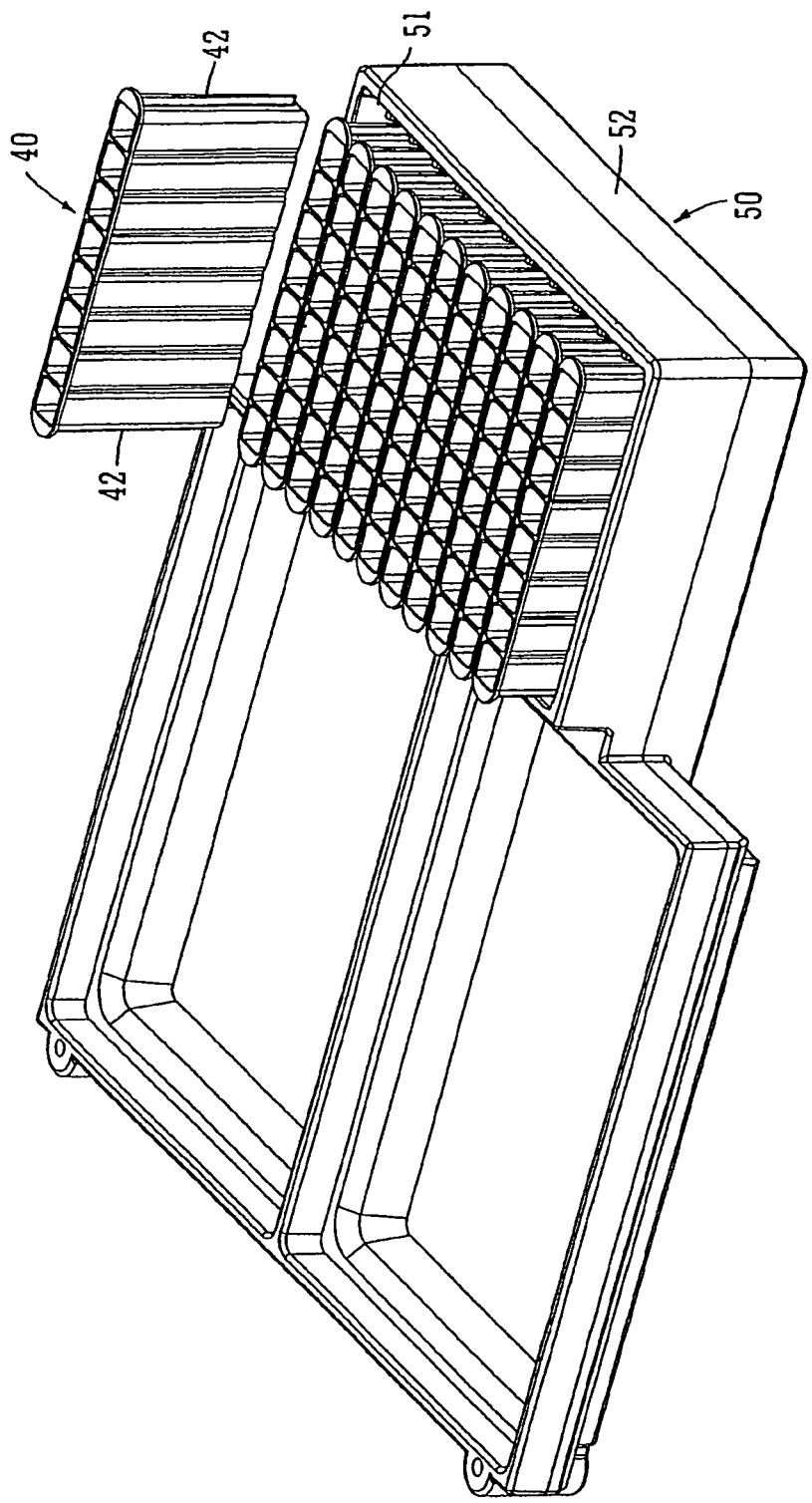

FIG. 8 shows a side view of the preferred immunoassay apparatus with the first or upper microtitre plate positioned in a fully forward position and the second or lower microtitre plate moving towards the rear of the apparatus with a guide wheel which is attached to the second or lower microtitre plate holder following a raised contoured path thereby causing the second or lower microtitre plate holder to be raised up as it approaches the reading device;

FIG. 9 shows a side view of the preferred immunoassay apparatus with the first or upper microtitre plate positioned in a fully forward position and the second or lower microtitre plate holder now having been raised up so that the second or lower microtitre plate passes through the reading device at substantially the same height as the first or upper microtitre plate;

FIG. 10 shows a side view of the preferred immunoassay apparatus with the first or upper microtitre plate positioned in a fully forward position and the second or lower microtitre plate having passed through the reading device and beginning to descend towards an incubator module which is positioned towards the rear of the apparatus;

FIG. 11 shows a side view of the preferred immunoassay apparatus with the first or upper microtitre plate positioned in a fully forward position and the second or lower microtitre plate positioned towards the rear of the apparatus in an incubator module;

FIG. 12 shows a side view of the preferred immunoassay apparatus with the second or lower microtitre plate positioned in a fully forward position and the first or upper microtitre plate being translated towards the rear of the apparatus with the first row of the first or upper microtitre plate passing through the reading device;

FIG. 13A shows a side sectional view of the preferred immunoassay apparatus showing two of the pivot arms and one of the guide wheels which in use are attached to a second or lower plate holder together with the optical transmitter and the optical receiver sections of the reader device and FIG. 13B shows in greater detail the various optical components comprising the reading device;

FIGS. 14A, 14B, and 14C show perspective views of a dilution strip according to an embodiment of the present invention;

FIG. 15A shows a plan view of a preferred dilution strip showing eight dilution wells arranged in a line, FIG. 15B shows an end-on side view of a preferred dilution strip showing a projection for engaging with a slot in a preferred dilution strip holder, FIG. 15C shows a side view of a preferred dilution strip showing a projection at either end of the dilution strip for engaging with a slot in a preferred dilution strip holder, FIG. 15D shows a cross-sectional view of a dilution well of the preferred dilution strip and FIG. 15E shows a transverse view of two wells of the preferred dilution strip;

FIG. 16 shows a dilution strip holder for holding a plurality of dilution strips according to a preferred embodiment of the present invention; and FIG. 17 shows eleven dilution strips loaded into a preferred dilution strip holder and a twelfth dilution strip positioned ready to be loaded into the preferred dilution strip holder.

Figure 1A:
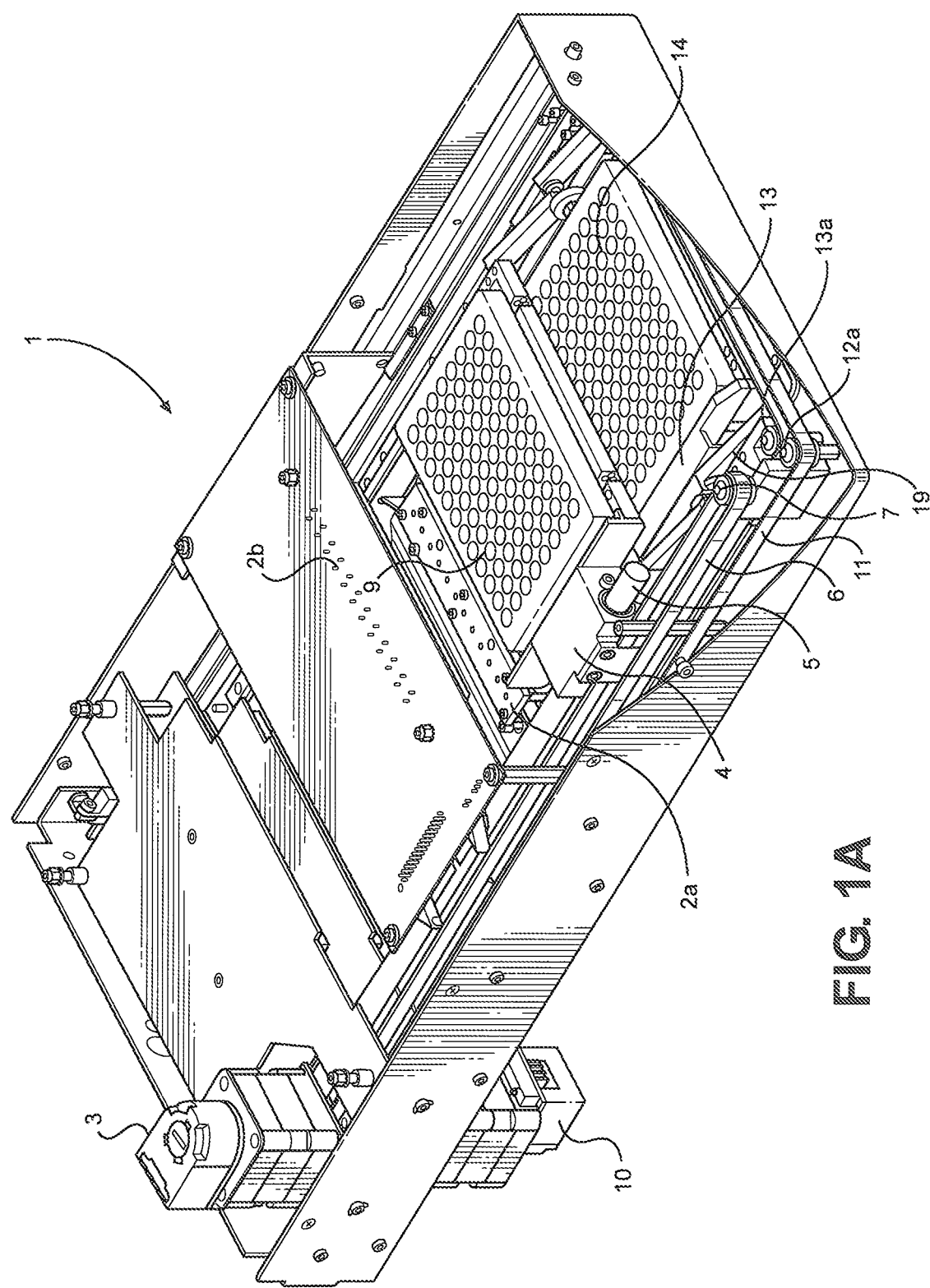

A first main preferred embodiment of the present invention relating to an immunoassay apparatus for reading two microtitre plates using a single reader device will now be described with reference to FIGS. 1-13B. FIG. 1 shows an automated immunoassay apparatus 1 according to a preferred embodiment which preferably comprises a single optical reading device 2a,2b for reading two microtitre plates 9,14. The microtitre plates 9,14 are preferably loaded at the front of the apparatus 1 and are preferably translated over or through the optical reading device 2a,2b in order to be read by the optical reading device 2a,2b. The optical reading device 2a,2b preferably comprises a strip or line of twelve photo-emitters or photodiodes 2a as shown in FIG. 1A. The light emitters are preferably positioned below a microtitre plate and the microtitre plate preferably passes above or over the light-emitters. A strip or line of photodiodes 2b is preferably arranged or positioned above the microtitre plate 9;14 which is being read. The photo-emitters or photodiodes 2a preferably emit a plurality of laser or light beams which preferably pass through the bottom of a row of wells of a microtitre plate 9;14. The light is preferably transmitted through the wells and is then preferably detected by the strip or line of photodiodes 2b. Immediately prior to reading a microtitre plate 9;14 a cover may be slid over a portion of the apparatus 1 in order to shield the reading device 2a,2b from ambient light.

Figure 1B:
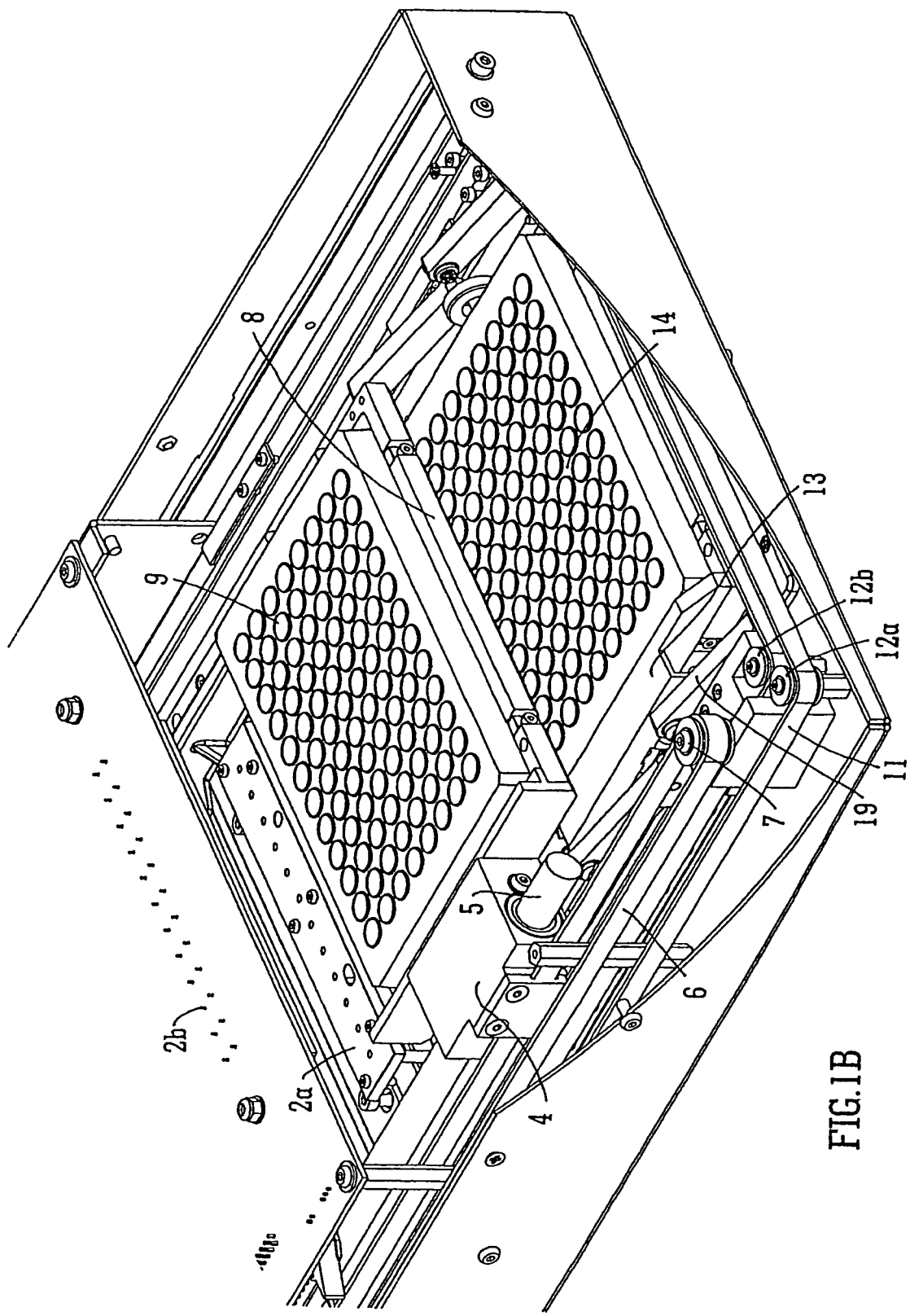

The preferred automated immunoassay apparatus 1 preferably comprises a first or upper plate drive mechanism for translating a first or upper microtitre plate 9 forwards and backwards through the apparatus 1. The first or upper plate drive mechanism is preferably arranged to pass the first or upper microtitre plate 9 through the reading device 2a,2b. The first or upper plate drive mechanism preferably comprises a first or upper plate drive motor 3, two first sliding devices or bearing blocks 4 which preferably slide along separate parallel guide rods 5 and a first or upper drive belt 6. The two first sliding devices or bearing blocks 4 (only one is shown in FIGS. 1A and 1B) preferably slide or otherwise translate along separate parallel guide rods 5 (again only one is partially shown in FIGS. 1A and 1B). The two first sliding device or bearing blocks 4 are preferably attached to the first or upper drive belt 6 and are also preferably attached to a first or upper microtitre plate holder 8. A first or upper microtitre plate 9 is preferably positioned or otherwise located in use in the first or upper microtitre plate holder 8. The first sliding devices or bearing blocks 4 and the first or upper microtitre plate holder 8 attached thereto is preferably driven by the first or upper belt 6. The first or upper drive belt 6 is preferably driven by the first or upper plate drive motor 3 and the first or upper drive belt 6 preferably passes around one or more first pulleys or spindles 7.

The first or upper microtitre plate 9 may initially be loaded into the first or upper plate holder 8 manually by the user. In a mode of operation the first or upper plate holder 8 is preferably linearly translated or otherwise moved, preferably at a substantially fixed or constant height, backwards and forwards along an axis of the apparatus 1 which preferably extends from the front of the apparatus 1 towards the rear of the apparatus 1. According to the preferred embodiment microtitres plates 9,14 may be loaded, processed and washed towards the front of the apparatus 1. The microtitre plates 9,14 may be read by the reading device 2a,2b towards the centre of the apparatus 1 and may be incubated in an incubator module located towards the rear of the apparatus 1.

The preferred automated immunoassay apparatus 1 preferably further comprises a second or lower plate drive mechanism. The second or lower plate drive mechanism preferably comprises a second or lower plate drive motor 10, two second sliding devices or bearing blocks 17, two linear guide tracks 18 and a second or lower drive belt 11. The second or lower drive belt 11 preferably extends in a substantially U-shaped arrangement (see FIG. 4) around one or more second pulleys or spindles from the rear of the apparatus 1, along one side of the apparatus 1, around the front of the apparatus 1 and back along the other side of the apparatus 1 to the rear of the apparatus 1.

A second or lower microtitre plate holder 13 which may be positioned or arranged at different vertical heights is preferably connected via four pivoting arms 19 to the two second sliding devices or bearing blocks 17 which preferably slide along the two linear guide tracks 18 and which are preferably driven by the second or lower drive belt 11.

The two second sliding devices or bearing blocks 17 preferably remain, in use, at a substantially constant or fixed horizontal height as they are preferably driven forwards and backwards by the second or lower drive belt 11 and are preferably guided along the length of the linear guide tracks 18. The two second sliding devices or bearing blocks 17 preferably engage the two linear guide rails or tracks 18. Attached to the two second sliding devices or bearing blocks 17 are four arms 19 which are preferably pivotally mounted or otherwise connected at one end to the two second sliding devices or bearing blocks 17. The arms 19 are preferably connected at an opposed end to the second or lower microtitre plate holder 13. A guide wheel 15 (see FIG. 5) is preferably attached either side of the second or lower microtitre plate holder 13.

According to the preferred embodiment the two second sliding devices or bearing blocks 17 are preferably moved forwards and backwards by the second or lower drive belt 11 which is preferably driven by the second or lower plate drive motor 10. As the two second sliding devices or bearing blocks 17 are driven forwards or backwards the guide wheels 15 on either side of the second or lower microtitre plate holder 13 preferably run along or otherwise follow a track 16 (see e.g. FIGS. 2 and 5) which preferably has a contoured profile. The track 16 preferably increases in height with a plateau region generally towards the centre or middle of the apparatus as can be seen more clearly from FIGS. 5-13B.

The contoured track 16 preferably has a profile such that the track 16 preferably starts increasing or ramping up in height about a third of the way along the axis of the apparatus as measured from the front of the apparatus towards the rear. The track 16 preferably plateaus in height in the centre or middle section of the apparatus 1 for approximately 20-25% of the axial length of the apparatus 1. The track 16 then preferably starts decreasing or ramping down in height towards the rear of the apparatus 1. Accordingly, as the two second sliding devices or bearing blocks 17 are driven by the second or lower belt 11 towards the centre of the apparatus 1, the guide wheels 15 on either side of the second or lower microtitre plate holder 13 preferably follow the contoured track 16. As the contoured track 16 begins to increase in height then the guide wheels 15 follow the contoured track 16 and so are also raised in height. As a result the attached second or lower microtitre plate holder 13 which is pivotally connected to the two second sliding devices or bearing blocks 17 by four pivoting arms 19 is also raised up. The second or lower microtitre plate holder 13 is kept horizontal by the four pivoting arms 19.

Figure 2:
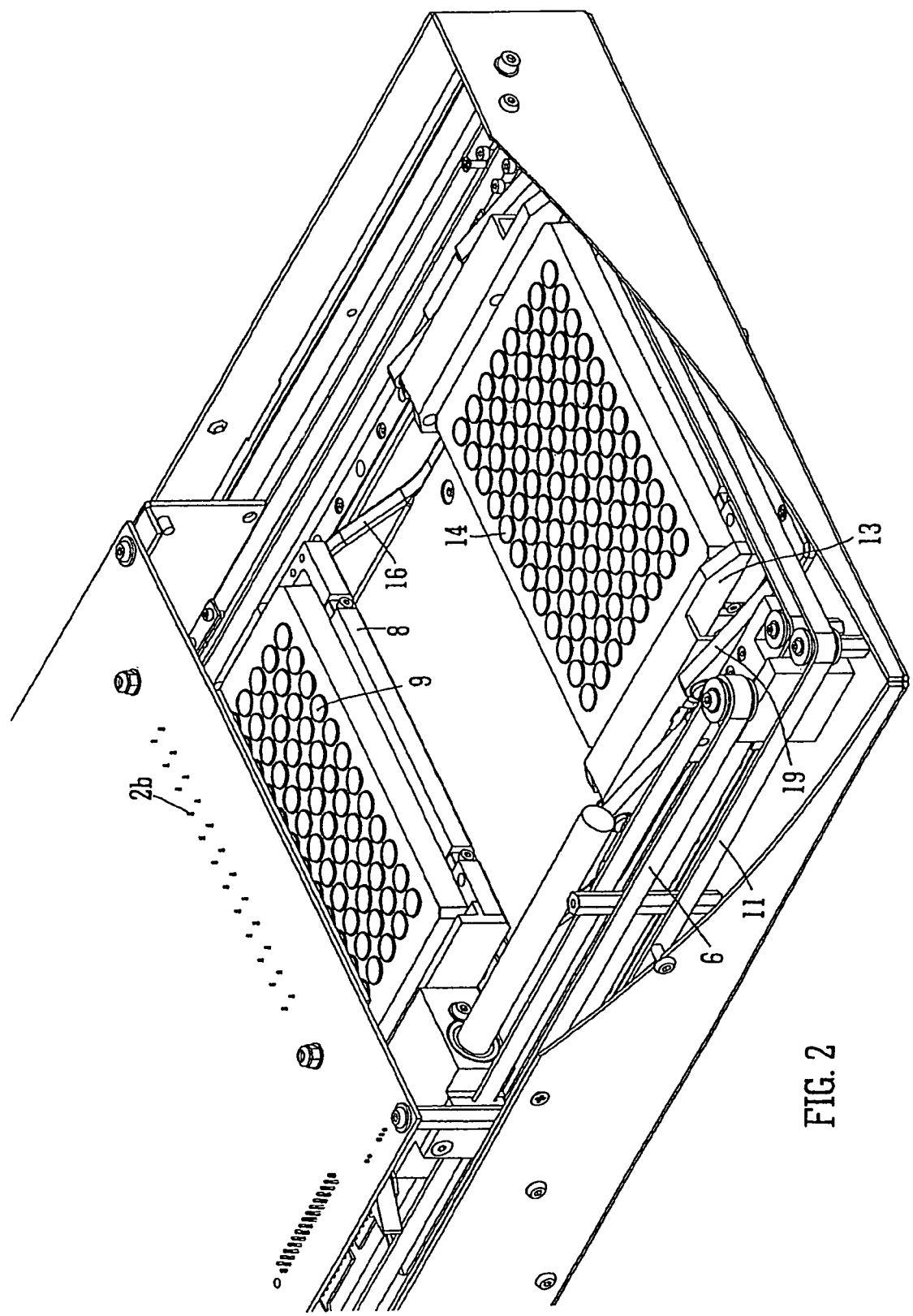
FIG. 2 shows the first or upper microtitre plate being translated towards the rear of the apparatus and passing through an optical reader positioned in the centre of the apparatus.

FIG. 2 shows in greater detail the first or upper microtitre plate holder 8 and a first or upper microtitre plate 9 positioned in the first or upper microtitre plate holder 8. A second or lower microtitre plate holder 13 is also shown with a second or lower microtitre plate 14 positioned in the second or lower microtitre plate holder 13. A part of the first or upper drive mechanism and a part of the second or lower drive mechanism is also shown.

Figure 3:
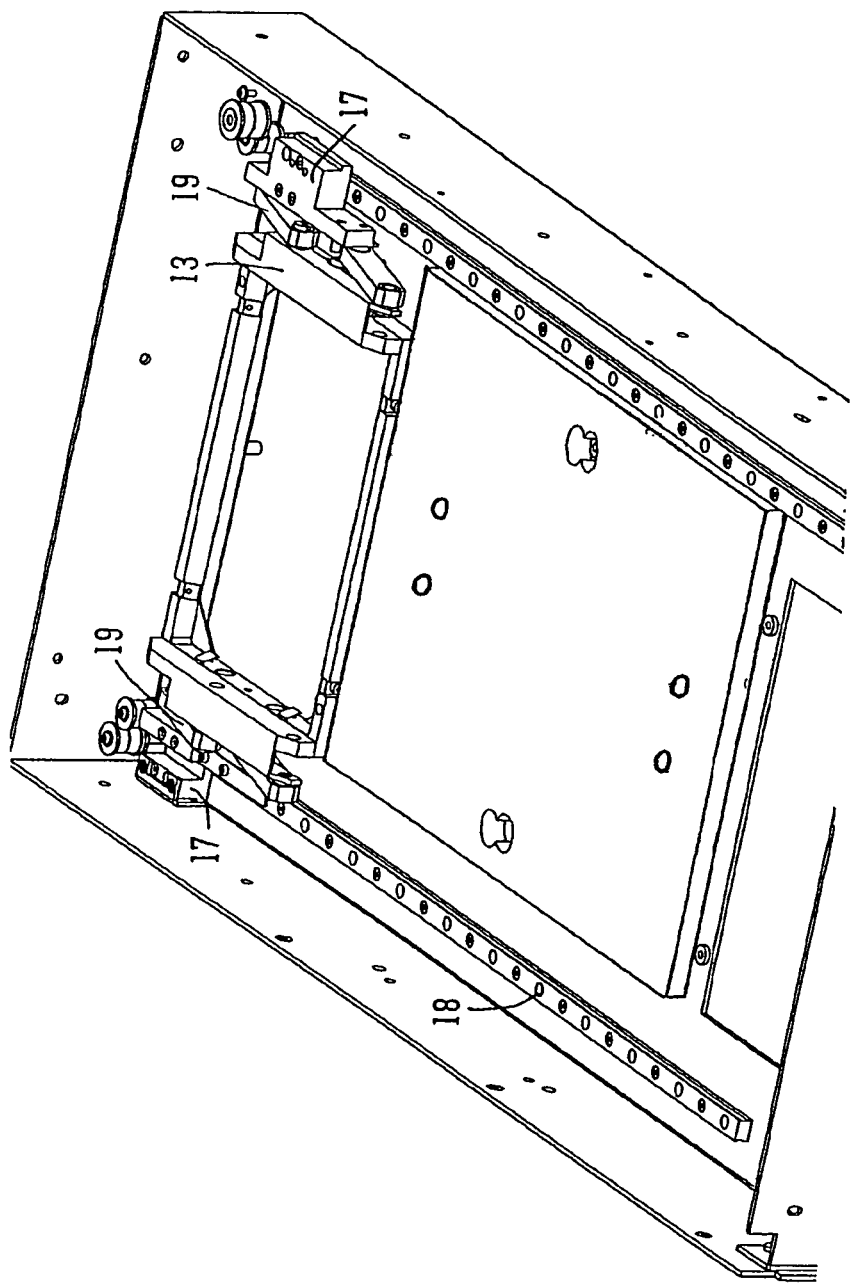
FIG. 3 shows a linear track guide mechanism along which two sliding devices or bearing blocks can slide, the two sliding devices or bearing blocks being connected to a second or lower microtitre plate holder via four pivoting arms.

FIG. 3 shows in more detail the two linear guide tracks 18 along which the two second sliding devices or bearing blocks 17 are driven by the second or lower drive belt 11.

Figure 4:
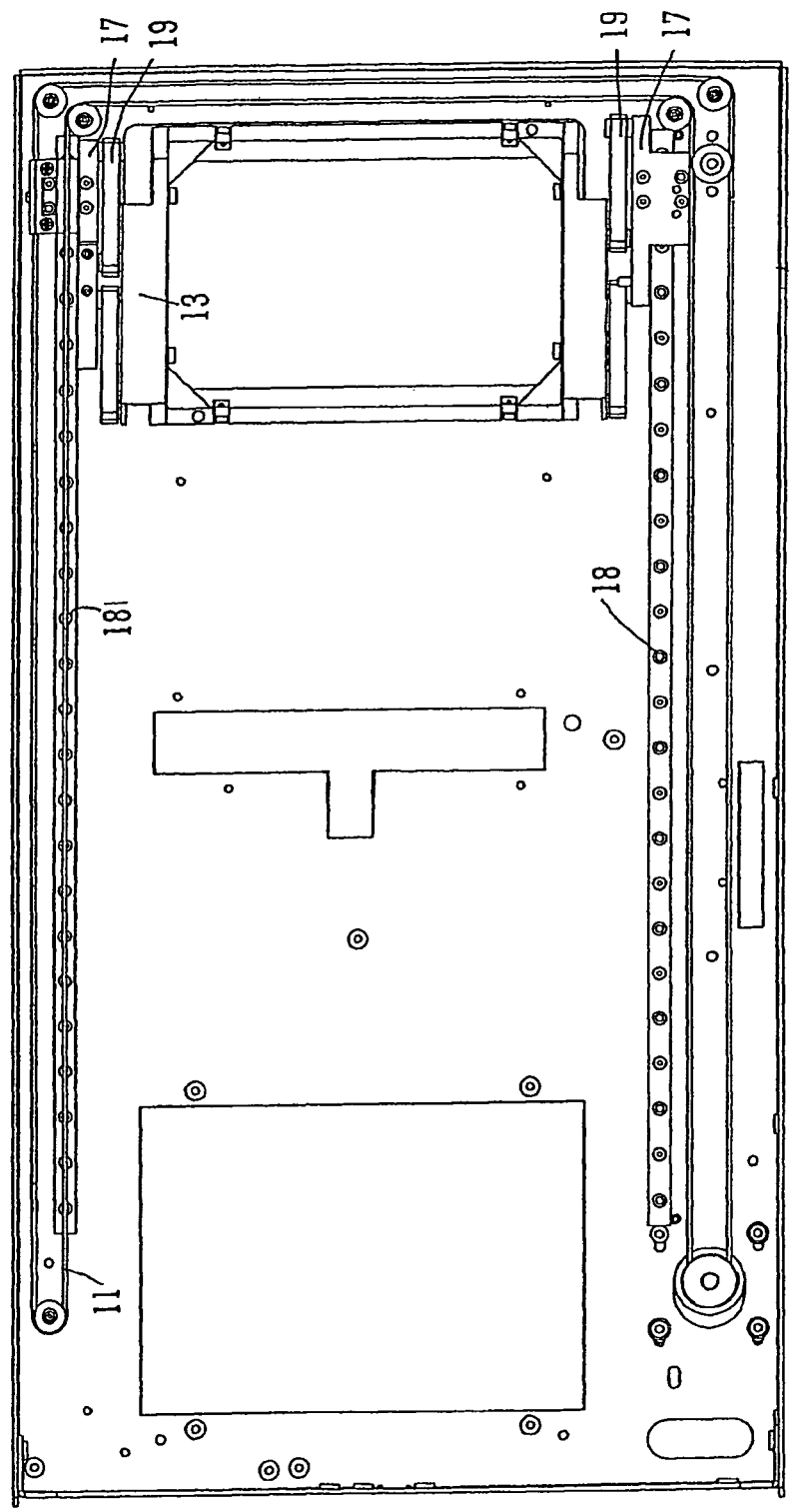
FIG. 4 shows a plan view of the linear track guide mechanism showing the two sliding devices or bearing blocks and a lower or second microtitre plate holder which is attached to the sliding devices or bearing blocks via four pivoting arms.

FIG. 4 shows a plan view showing the two linear guide tracks 18 which guide the two second sliding devices or bearing blocks 17 when they are driven by the second or lower drive belt 11.

Towards the rear of the apparatus an incubator module is preferably provided. The incubator module is not shown in FIGS. 1-4 but is shown in more detail in FIGS. 5-13A.

Figure 5:
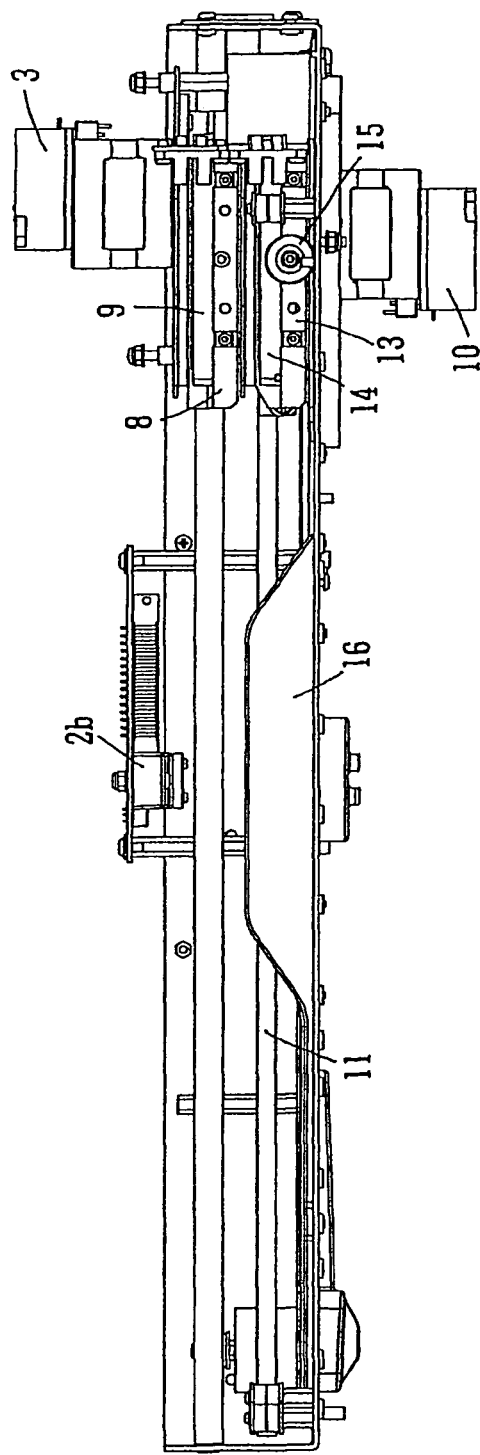
FIG. 5 shows a side view of the preferred immunoassay apparatus with the first or upper microtitre plate and the second or lower microtitre plate positioned towards the rear of the apparatus in an incubator module.

FIG. 5 shows the first or upper microtitre plate 9 and the second or lower microtitre plate 14 located in a home position wherein the first or upper microtitre plate 9 is positioned in an incubator module which is preferably located towards the rear of the apparatus 1 and wherein the second or lower microtitre plate 14 is also positioned in the incubator module. The second or lower microtitre plate 14 is preferably positioned or stacked below the first or upper microtitre plate 9 in the incubator module.

Figure 6:
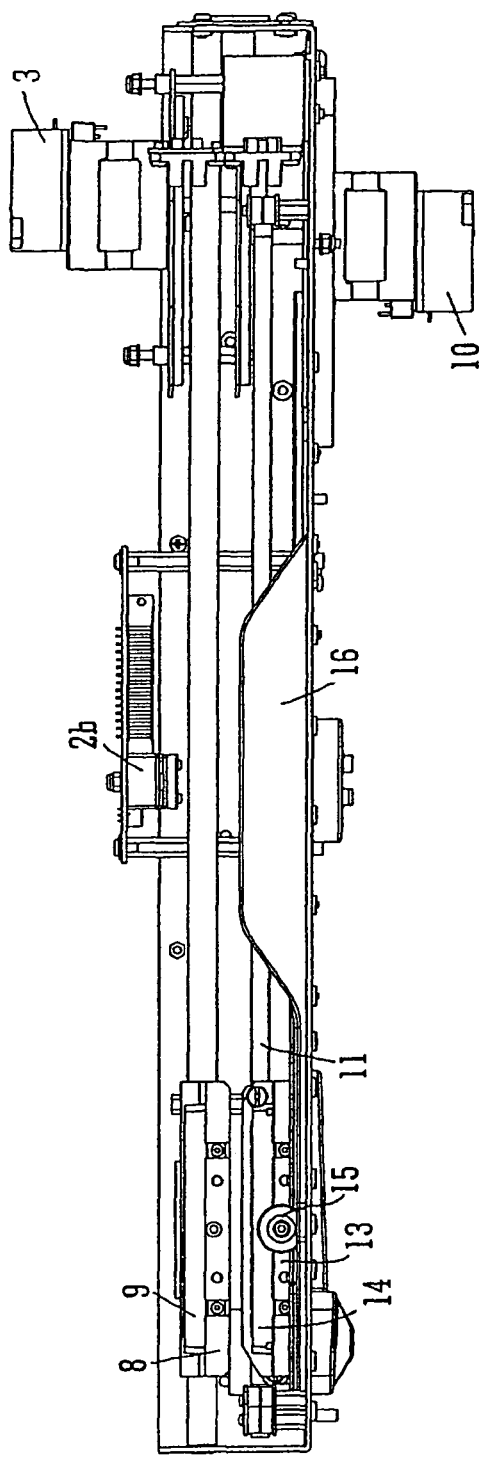
FIG. 6 shows a side view of the preferred immunoassay apparatus with the first or upper microtitre plate and the second or lower microtitre plate positioned towards the front of the apparatus such that the first or upper microtitre plate is accessible to a robotic arm for pipetting or washing.

FIG. 6 shows the first or upper microtitre plate 9 and the second or lower microtitre plate 14 positioned towards the front of the apparatus 1 such that the first or upper microtitre plate 9 is generally accessible to a robotic arm for pipetting or washing.

Figure 7:
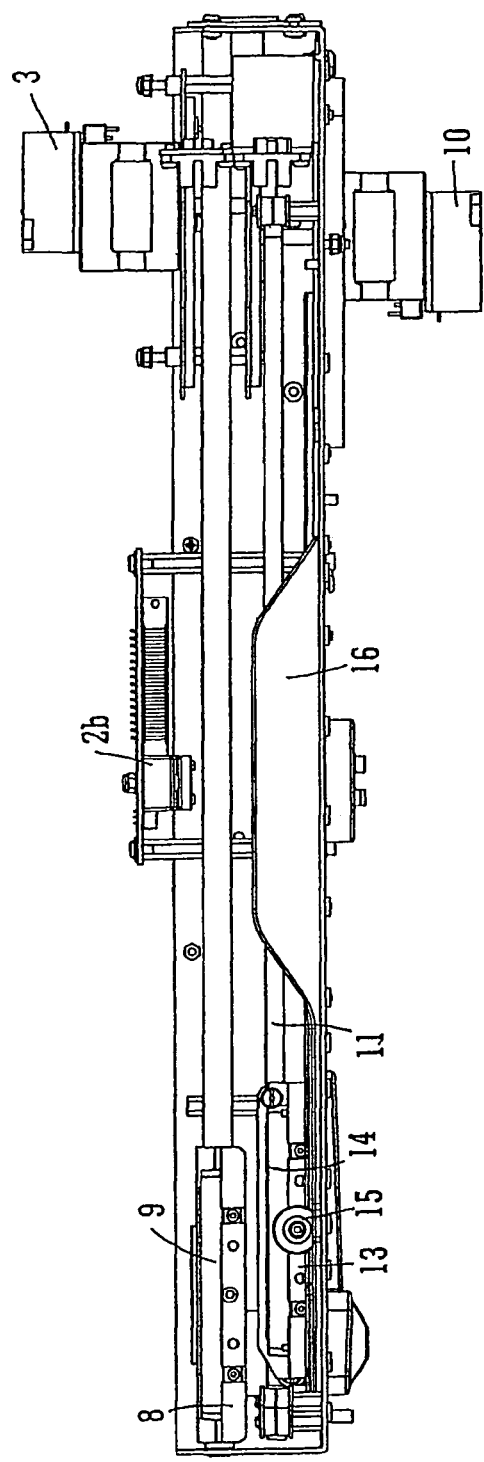
FIG. 7 shows a side view of the preferred immunoassay apparatus with the first or upper microtitre plate positioned in a fully forward position which allows the second or lower microtitre plate to move out from underneath the first or upper microtitre plate.

FIG. 7 shows the first or upper microtitre plate 9 in a fully forward position which allows or enables the second or lower microtitre plate 14 to move out from underneath the first or upper microtitre plate 9.

FIG. 8 shows the first or upper microtitre plate 9 in a fully forwards position and the second or lower microtitre plate 14 beginning to move towards the centre of the apparatus 1.

The contoured track 16 is preferably arranged such that when the two second sliding devices or bearing blocks 17 are driven towards the centre of the apparatus 1 the two guide wheels 15 attached to either side of the second or lower microtitre plate holder 13 follow the contoured track 16 and preferably begin to move up the slope or ramp of the contoured track 16 as shown in FIG. 8. As the guide wheels 16 move up or otherwise follow the contoured track or ramp 16, the second or lower plate holder 13 attached to the two guide wheels 15 preferably becomes raised up and is preferably kept substantially horizontal by the four pivot arms 19.

The optical reading device 2a,2b is preferably positioned at or towards the centre of the apparatus 1 and/or at or towards the centre of the contoured track 16. The reading device 2a,2b preferably comprises an array of light-emitters 2a which are preferably located so as to be below the position of a microtitre plate 9,14 when it is being read. The optical reading device 2a,2b preferably also comprises an array of photodiodes 2b which are preferably positioned or arranged above the position of a microtitre plate 9,14 when it is being read. According to an alternative less preferred embodiment, the array of light-emitters may be located above the position of a microtitre plate when it is being read and an array of photodiodes may be positioned below the position of a microtitre plate when it is being read.

FIG. 9 shows the first or upper microtitre plate 9 in a fully forward position and the second or lower microtitre plate 14 having been raised up so that the guide wheels 15 travel along a plateau region of the contoured track 16. The second or lower microtitre plate 9 is preferably positioned so as to be at reading height for the reading optics of the reading device 2a,2b. The second or lower microtitre plate 14 is shown in FIG. 9 in a position wherein the first row of the second or lower microtitre plate 14 is in a position ready to be read by the reading device 2a,2b.

FIG. 10 shows the first or upper microtitre plate 9 in a fully forward position and the second or lower microtitre plate 14 having passed through the reading device 2 and now beginning to descend towards the rear of the apparatus 1. The two guide wheels 15 are positioned on the rear ramp or rear profile or slope of the contoured track 16.

FIG. 11 shows the first or upper microtitre plate 9 in a fully forward position and the second or lower microtitre plate 15 having been fully lowered in height and now positioned within an incubator module which is located at or towards the rear of the apparatus 1.

FIG. 12 shows the second or lower microtitre plate 14 in a fully forward position and the first or upper microtitre plate 9 being translated towards the rear of the apparatus and in a position wherein the first row of wells in the first or upper microtitre plate 9 is in a position so as to be read by the reading device 2a,2b.

FIG. 13A shows a cross-sectional view through the reading device 2a,2b and shows the various components of the optical transmitter 2a and the optical receiver 2b. FIG. 13B shows in greater detail the optical components of the optical transmitter 2a and the optical receiver 2b. The optical transmitter 2a preferably comprises a lamp, an infra-red heat filter, a lens and a filter. The filtered light then preferably passes through a plurality of optic fibres which preferably provide a plurality of light beams having a desired profile. Each light beam preferably passes through one of a plurality of lower lenses and a plurality of lower optical stops. The light beams will then pass through a row of wells of a microtitre plate. The optical receiver 2b located above the microtitre plate being read preferably comprises a plurality of upper optical stops, a plurality of upper lenses and a plurality of photodiodes. An upper optical step, an upper lens and a photodetector are preferably provided per optical beam or channel.

A second main preferred embodiment of the present invention relates to a dilution strip and a dilution strip holder. This embodiment will now be described with reference to FIGS. 14-17. FIG. 14 shows a dilution strip 40 according to an embodiment of the present invention. The dilution strip 40 preferably comprises a line or array of dilution wells 41a, 41b . . . 41h preferably arranged in an 8×1 format. Other less preferred embodiments are contemplated wherein the dilution strip may have a different format, e.g. a 12×1 format. The dilution strip 40 preferably has an overall length of approximately 79.9 mm, an overall width of 10 mm and an overall height of 39.8 mm. The centre to centre spacing of the eight dilution wells 41a,41b . . . 41h is preferably 9.0 mm. Each dilution well 41a,41b . . . 41h preferably has a substantially square cross-sectional profile which may taper towards the bottom of the well. According to an embodiment each dilution well may preferably be 8.0 mm×8.0 mm wide at the top and may taper to being 7.4 mm×7.4 mm wide at a height 3.9 mm above the bottom of the well. The base or bottom portion of each dilution well preferably comprises an inverted four sided pyramid. The inverted four sided pyramid preferably has a height or depth of 3.9 mm. The dilutions wells may according to one embodiment have a mean cross-sectional area of 58.4 $mm^2$. The height of the dilution wells above the inverted four sided pyramid base or bottom portion is preferably 34.6 mm. The ratio between the average width and the height of each dilution well is preferably 1:4.6. The maximum volume of each dilution well is preferably 2.11 ml. According to a less preferred embodiment the base of each dilution well 41a,41b . . . 41h may be rounded or flat.

FIG. 15A shows a plan view of a dilution strip 40 according to the preferred embodiment. FIG. 15B shows a side end-on view of a preferred dilution strip 40. According to a preferred embodiment the preferred dilution strip 40 preferably has two projections 42 on either side which preferably run 38.8 mm below a 1.0 mm lip 43. The projections 42 preferably engage in use with a slot, slit or groove 51 provided in a dilution strip holder 50 as shown in FIG. 18.

FIG. 15C shows a side view of a preferred dilution strip 40 and shows the lip 43 and the two side projections 42.

FIG. 15D shows a cross-sectional view of a first dilution well 41a of the preferred dilution strip 40 and shows the profile of the base of the dilution well 41a according to an embodiment. FIG. 15E shows a transverse section along the first two dilution wells 41a,41b of the preferred dilution strip 40.

FIG. 16 shows a dilution strip holder 50 according to an embodiment of the present invention. The dilution strip holder 50 preferably comprises a tray 52 with a plurality of slits or slots 51 along two sides for receiving the projections 42 of a preferred dilution strip 40.

FIG. 17 shows eleven dilution strips 40 loaded, mounted or otherwise held in a preferred dilution strip holder 50. A twelfth dilution strip 40 is shown positioned ready to be inserted or slotted into the preferred dilution strip holder 50. A dilution strip 40 is preferably loaded by engaging the two projections 42 on either side of the preferred dilution strip 40 with the two slots, slits or grooves 51 in the preferred dilution strip holder 50. The dilution strip holder, 50 preferably has a length of approximately 134.5 mm, a width of approximately 91.75 mm and a height of approximately 35.50 mm Although the present invention has been described with reference to preferred embodiments, it will be understood by those skilled in the art that various changes in form and detail may be made without departing from the scope of the present invention as set forth in the accompanying claims.

The invention claimed is:

1. An automated immunoassay apparatus comprising:
a first mechanism for moving a first microtitre plate holder adapted to carry a first microtitre plate;
a second mechanism for moving a second microtitre plate holder having one or more guide wheels attached thereto and being adapted to carry a second microtitre plate, wherein said second mechanism comprises one or more linear guide tracks or rails and one or more sliding devices which are configured to translate along said one or more linear guide tracks or rails in a first direction;
one or more pivoting arms connecting said one or more sliding devices to said second microtitre plate holder;
a single reading device configured to read first and second microtitre plates carried by the first and second microtitre plate holders respectively; and
a contoured track, said one or more guide wheels being arranged to follow said contoured track in a second direction;
wherein one of the first or second directions functions to raise and lower the second microtitre plate holder in height.

2. The automated immunoassay apparatus as claimed in claim 1, wherein said first mechanism comprises a drive mechanism for selectively translating said first microtitre plate holder forwards or backwards along a longitudinal axis, wherein said first mechanism is configured to maintain said first microtitre plate holder at substantially a constant height along at least 5%, 10%, 15%, 20%, 25%, 30%, 35%, 40%, 45%, 50%, 55%, 60%, 65%, 70%, 75%, 80%, 85%, 90%, 95% or 100% of the length of said longitudinal axis.

3. The automated immunoassay apparatus as claimed in claim 1, wherein said first mechanism comprises one or more linear guide tracks or rails and one or more sliding devices which are configured to translate along said one or more linear guide tracks or rails.

4. The automated immunoassay apparatus as claimed in claim 3, further comprising a first microtitre plate positioned on said first microtitre plate holder.

5. The automated immunoassay apparatus as claimed in claim 1, wherein said second mechanism comprises a drive mechanism for selectively translating said second microtitre plate holder forwards or backwards along a longitudinal axis, wherein said second mechanism is arranged and adapted to vary the height of said second microtitre plate holder along at least 5%, 10%, 15%, 20%, 25%, 30%, 35%, 40%, 45%, 50%, 55%, 60%, 65%, 70%, 75%, 80%, 85%, 90%, 95% or 100% of a length of said longitudinal axis.

6. The automated immunoassay apparatus as claimed in claim 1, further comprising a drive motor for translating said one or more sliding devices and said second microtitre plate holder.

7. The automated immunoassay apparatus as claimed in claim 1, wherein said one or more pivoting arms comprise four pivoting arms which form a parallelogram with said second microtitre plate holder and said one or more sliding devices.

8. The automated immunoassay apparatus as claimed in claim 1, wherein said one or more pivoting arms are configured to ensure that said second microtitre plate holder remains substantially horizontal during translation.

9. The automated immunoassay apparatus as claimed in claim 1, wherein said contoured track in combination with said one or more guide wheels is arranged to cause said second microtitre plate holder to be raised and lowered in height and wherein said contoured track has a substantially horizontal region, a first ramp portion connected to a first side of said substantially horizontal region and a second ramp portion connected to a second side of said substantially horizontal region.

10. A method of reading microtitre plates comprising:
using a first mechanism to translate a first microtitre plate holder relative to a single reading device, the first microtitre plate holder carrying a first microtitre plate;
using a second mechanism to translate a second microtitre plate holder relative to said single reading device, wherein said second mechanism comprises one or more linear guide tracks or rails and one or more sliding devices which are configured to translate along said one or more linear guide tracks or rails, and wherein one or more pivoting arms connect said one or more sliding devices to said second microtitre plate holder;
positioning a second microtitre plate on said second microtitre plate holder;
directing one or more guide wheels attached to said second microtitre plate holder to follow a contoured track to cause said second microtitre plate holder to be raised and lowered in height; and
reading said first microtitre plate and said second microtitre plate using said single reading device.

11. An assay apparatus comprising:
one or more first sliding devices for sliding along one or more linear guide tracks or rails, said one or more first sliding devices being attached to a first microtitre plate holder; and
one or more second sliding devices for sliding along one or more linear guide tracks or rails, said one or more second sliding devices being connected to a second microtitre plate holder via one or more pivoting arms, wherein a height of said second microtitre plate holder may be varied during sliding of the one or more second sliding devices;
wherein second microtitre plate holder comprises one or more guide wheels for engaging with one or more guides, wherein said one or more guides have a vertical profile which varies along an axial length of said one or more guides and wherein when said one or more guide wheels engage with said one or more guides, a vertical height of said second microtitre plate is caused to vary.

12. The assay apparatus as claimed in claim 11, wherein said first microtitre plate holder and said second microtitre plate holder are arranged to pass by a common reading device, said reading device being arranged to measure an optical density of samples in a first microtitre plate loaded on said first microtitre plate holder and a second microtitre plate loaded on said second microtitre plate holder.

* * * * *